(12) United States Patent
Hermann et al.

(10) Patent No.: US 8,795,145 B2
(45) Date of Patent: Aug. 5, 2014

(54) BRACHYTHERAPY APPARATUS AND METHODS FOR USING SAME

(75) Inventors: George D. Hermann, Portola Valley, CA (US); Gail S. Lebovic, McKinney, TX (US)

(73) Assignee: Cianna Medical, Inc., Aliso Viejo ( * ) Notice: Subject to any disclaimer, the term of this patent is extended or adjusted under 35 U.S.C. 154(b) by 1401 days.

(21) Appl. No.: 12/437,534

(22) Filed: May 7, 2009

(65) Prior Publication Data

US 2009/0216064 A1    Aug. 27, 2009

Related U.S. Application Data

(63) Continuation of application No. 10/658,518, filed on Sep. 9, 2003, now Pat. No. 7,601,113.

(60) Provisional application No. 60/409,449, filed on Sep. 10, 2002.

(51) Int. Cl.
*A61N 5/00*    (2006.01)

(52) U.S. Cl.
USPC .............................................................. 600/3

(58) Field of Classification Search
USPC ...................................................... 600/1–8
See application file for complete search history.

(56) References Cited

U.S. PATENT DOCUMENTS

| | | |
|---|---|---|
| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |
| 4,706,652 A | 11/1987 | Horowitz |
| 4,714,074 A | 12/1987 | Rey et al. |
| 4,798,212 A | 1/1989 | Arana |
| 4,936,823 A | 6/1990 | Colvin et al. |
| 4,957,476 A | 9/1990 | Cano |
| 4,976,680 A | 12/1990 | Hayman et al. |
| 5,056,523 A | 10/1991 | Hotchkiss, Jr. et al. |
| 5,106,360 A | 4/1992 | Ishiwara et al. |
| 5,152,741 A | 10/1992 | Farnio |
| 5,235,966 A | 8/1993 | Jamner |
| 5,242,372 A | 9/1993 | Carol |
| 5,279,565 A | 1/1994 | Klein et al. |

(Continued)

FOREIGN PATENT DOCUMENTS

| | | |
|---|---|---|
| EP | 0318447 B1 | 9/1994 |
| EP | 0390528 B1 | 1/1997 |

(Continued)

OTHER PUBLICATIONS

Agent for and European Patent Examiner, Office Actions and Responses for European Patent Application No. 03759230.0, dated May 9, 2006 to Mar. 17, 2008, Applicant: Curay Medical, Inc., 35 pages.

*Primary Examiner* — Samuel Gilbert
(74) *Attorney, Agent, or Firm* — Vista IP Law Group LLP; William A. English

(57) ABSTRACT

Apparatus, systems and methods are provided for delivering brachytherapy to a target tissue region of a human or other mammalian body. A flexible brachytherapy device may be implanted that includes a therapy delivery portion having one or more radioactive sources securely retained thereto, and a tail portion extending from the therapy delivery portion. Once implanted, the tail portion may extend outside the body, where it may be folded and secured flat against the skin. The device may be removed at therapy completion.

30 Claims, 16 Drawing Sheets

(56) References Cited

U.S. PATENT DOCUMENTS

| | | | |
|---|---|---|---|
| 5,302,168 A | 4/1994 | Hess | |
| 5,336,178 A | 8/1994 | Kaplan et al. | |
| 5,354,257 A | 10/1994 | Roubin et al. | |
| 5,411,466 A | 5/1995 | Hess | |
| 5,423,747 A | 6/1995 | Amano | |
| 5,429,605 A | 7/1995 | Richling et al. | |
| 5,460,592 A * | 10/1995 | Langton et al. | 600/7 |
| 5,484,384 A | 1/1996 | Fearnot | |
| 5,503,613 A | 4/1996 | Weinberger | |
| 5,509,900 A | 4/1996 | Kirkman | |
| 5,538,502 A | 7/1996 | Johnstone | |
| 5,540,659 A | 7/1996 | Teirstein | |
| 5,611,767 A | 3/1997 | Williams | |
| 5,653,683 A | 8/1997 | D'Andrea | |
| 5,678,572 A | 10/1997 | Shaw et al. | |
| 5,707,332 A | 1/1998 | Weinberger | |
| 5,713,828 A | 2/1998 | Coniglione | |
| 5,720,717 A | 2/1998 | D'Andrea | |
| 5,730,698 A | 3/1998 | Fischell et al. | |
| 5,782,740 A | 7/1998 | Schneiderman | |
| 5,840,008 A | 11/1998 | Klein et al. | |
| 5,843,163 A | 12/1998 | Wall | |
| 5,851,171 A | 12/1998 | Gasson | |
| 5,863,284 A | 1/1999 | Klein | |
| 5,882,291 A | 3/1999 | Bradshaw et al. | |
| 5,891,091 A | 4/1999 | Teirstein | |
| 5,910,102 A | 6/1999 | Hastings | |
| 5,913,813 A | 6/1999 | Williams et al. | |
| 5,916,143 A | 6/1999 | Apple et al. | |
| 5,924,973 A * | 7/1999 | Weinberger | 600/3 |
| 5,931,774 A | 8/1999 | Williams et al. | |
| 5,938,582 A | 8/1999 | Ciamacco, Jr. et al. | |
| 5,942,209 A | 8/1999 | Leavitt et al. | |
| 5,976,106 A | 11/1999 | Verin et al. | |
| 6,013,019 A | 1/2000 | Fischell et al. | |
| 6,022,308 A | 2/2000 | Williams | |
| 6,030,333 A | 2/2000 | Sioshansi et al. | |
| 6,033,357 A | 3/2000 | Ciezki et al. | |
| 6,036,632 A | 3/2000 | Whitmore et al. | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Ganbale et al. | |
| 6,083,148 A | 7/2000 | Williams | |
| 6,110,164 A * | 8/2000 | Vidlund | 604/524 |
| 6,117,064 A | 9/2000 | Apple et al. | |
| 6,159,139 A | 12/2000 | Chiu | |
| 6,159,141 A | 12/2000 | Apple et al. | |
| 6,176,821 B1 | 1/2001 | Crocker et al. | |
| 6,179,766 B1 | 1/2001 | Dickerson | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,217,585 B1 | 4/2001 | Houser et al. | |
| 6,221,003 B1 | 4/2001 | Sierocuk et al. | |
| 6,221,030 B1 | 4/2001 | Avaltroni | |
| 6,234,951 B1 | 5/2001 | Hastings | |
| 6,238,374 B1 | 5/2001 | Winkler | |
| 6,251,060 B1 * | 6/2001 | Hooft et al. | 600/3 |
| 6,258,099 B1 | 7/2001 | Mareiro et al. | |
| 6,261,320 B1 | 7/2001 | Tam et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,287,249 B1 | 9/2001 | Tam et al. | |
| 6,338,709 B1 | 1/2002 | Geoffrion | |
| 6,358,195 B1 | 3/2002 | Green et al. | |
| 6,371,904 B1 | 4/2002 | Sirimanne et al. | |
| 6,413,204 B1 | 7/2002 | Winkler et al. | |
| 6,458,069 B1 | 10/2002 | Tam et al. | |
| 6,482,142 B1 | 11/2002 | Winkler et al. | |
| 6,482,178 B1 | 11/2002 | Andrews et al. | |
| 6,494,824 B1 | 12/2002 | Apple et al. | |
| 6,506,145 B1 | 1/2003 | Bradshaw et al. | |
| 6,508,784 B1 | 1/2003 | Shu | |
| 6,527,692 B1 | 3/2003 | Weinberger | |
| 6,527,693 B2 | 3/2003 | Munro, III et al. | |
| 6,540,656 B2 | 4/2003 | Fontayne et al. | |
| 6,540,734 B1 | 4/2003 | Chiu et al. | |
| 6,554,757 B1 | 4/2003 | Geitz | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,607,476 B1 | 8/2003 | Barnhart | |
| 6,607,478 B2 | 8/2003 | Williams | |
| 6,638,206 B2 | 10/2003 | Green et al. | |
| 6,641,518 B2 | 11/2003 | Wolfson et al. | |
| 6,645,135 B1 | 11/2003 | Bhat | |
| 6,648,811 B2 | 11/2003 | Sierocuk et al. | |
| 6,659,933 B2 | 12/2003 | Asano | |
| 6,673,006 B2 | 1/2004 | Winkler | |
| 6,676,667 B2 | 1/2004 | Mareiro et al. | |
| 6,685,619 B2 | 2/2004 | Halpern et al. | |
| 6,692,460 B1 | 2/2004 | Jayaraman | |
| 6,699,170 B1 | 3/2004 | Crocker et al. | |
| 6,746,465 B2 | 6/2004 | Diederich et al. | |
| 6,752,752 B2 | 6/2004 | Geitz | |
| 6,910,999 B2 | 6/2005 | Chin et al. | |
| 6,923,754 B2 | 8/2005 | Lubock | |
| 6,955,641 B2 | 10/2005 | Lubock | |
| 7,041,047 B2 | 5/2006 | Gellman et al. | |
| 7,056,276 B2 | 6/2006 | Nakano et al. | |
| 7,357,770 B1 | 4/2008 | Cutrer et al. | |
| 2001/0007071 A1 | 7/2001 | Koblish | |
| 2002/0016583 A1 | 2/2002 | Cragg | |
| 2002/0032359 A1 | 3/2002 | Geoffrion et al. | |
| 2002/0165427 A1 | 11/2002 | Yachia et al. | |
| 2003/0092957 A1 | 5/2003 | Scott et al. | |
| 2003/0114878 A1 | 6/2003 | Diederich et al. | |
| 2003/0158515 A1 | 8/2003 | Gonzalez et al. | |
| 2003/0163017 A1 | 8/2003 | Tam et al. | |
| 2003/0236443 A1 | 12/2003 | Cespedes et al. | |
| 2004/0006305 A1 | 1/2004 | Hebert et al. | |
| 2004/0068231 A1 | 4/2004 | Blondeau | |
| 2004/0087828 A1 | 5/2004 | Green et al. | |
| 2004/0116767 A1 | 6/2004 | Lebovic et al. | |
| 2004/0127765 A1 | 7/2004 | Seiler et al. | |
| 2004/0260142 A1 | 12/2004 | Lovoi | |
| 2005/0061533 A1 | 3/2005 | Lovoi | |
| 2005/0075662 A1 | 4/2005 | Pederson et al. | |
| 2005/0080313 A1 | 4/2005 | Stewart et al. | |
| 2005/0090845 A1 | 4/2005 | Boyd | |
| 2005/0096647 A1 | 5/2005 | Steinke et al. | |
| 2005/0101823 A1 | 5/2005 | Linares et al. | |
| 2005/0101860 A1 | 5/2005 | Patrick et al. | |
| 2005/0124843 A1 | 6/2005 | Singh | |
| 2005/0182286 A1 | 8/2005 | Lubock | |
| 2005/0240074 A1 | 10/2005 | Lubock | |
| 2006/0015166 A1 | 1/2006 | Kindlein et al. | |
| 2006/0020156 A1 | 1/2006 | Shukla | |
| 2006/0094923 A1 | 5/2006 | Mate | |
| 2006/0100475 A1 | 5/2006 | White | |
| 2006/0116546 A1 | 6/2006 | Eng | |
| 2006/0173233 A1 | 8/2006 | Lovoi | |
| 2006/0173235 A1 | 8/2006 | Lim et al. | |
| 2006/0184192 A1 | 8/2006 | Markworth et al. | |
| 2006/0199990 A1 | 9/2006 | Rioux et al. | |
| 2006/0235365 A1 | 10/2006 | Terwilliger et al. | |
| 2006/0258895 A1 | 11/2006 | Maschke | |

FOREIGN PATENT DOCUMENTS

| | | |
|---|---|---|
| EP | 0775505 | 5/1997 |
| EP | 0536888 B1 | 1/1998 |
| EP | 0955071 | 11/1999 |
| EP | 0884977 B1 | 4/2003 |
| EP | 0782410 B1 | 12/2003 |
| EP | 0955071 | 2/2004 |
| EP | 1402922 | 3/2004 |
| EP | 1405600 | 4/2004 |
| EP | 0808129 B1 | 5/2004 |
| EP | 1428477 | 6/2004 |
| EP | 1568397 | 8/2005 |

(56) References Cited

FOREIGN PATENT DOCUMENTS

| WO | 00/59378 | 10/2000 |
| WO | 01/95808 | 12/2001 |
| WO | 03/077768 | 9/2003 |
| WO | 03/079907 | 10/2003 |
| WO | 2005037363 | 4/2005 |

* cited by examiner

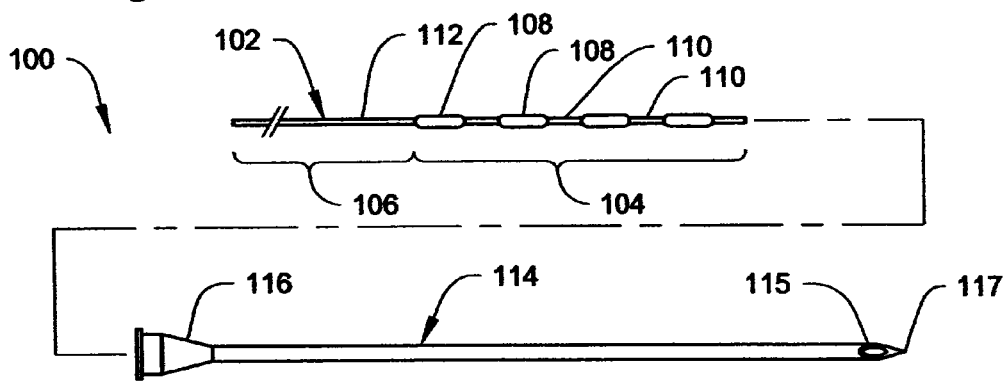
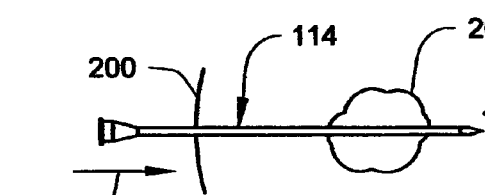
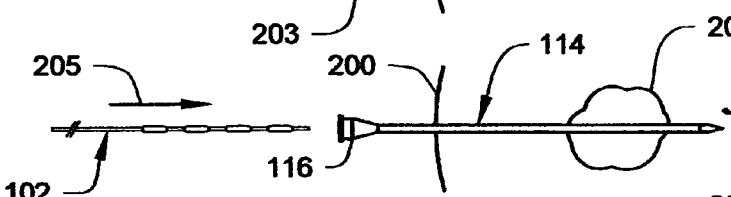
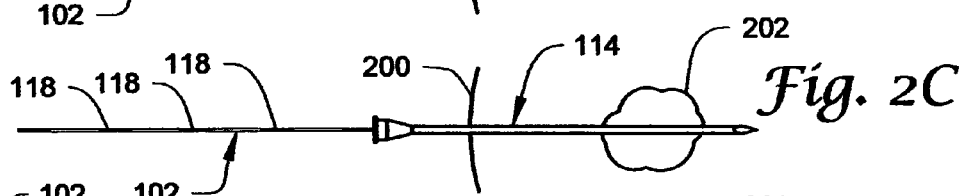
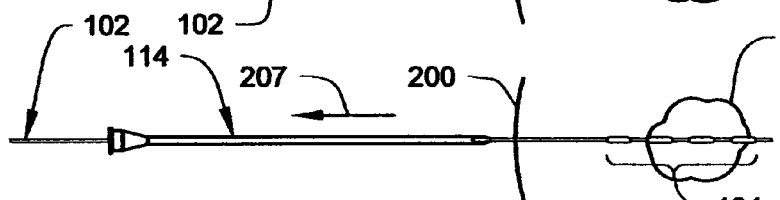
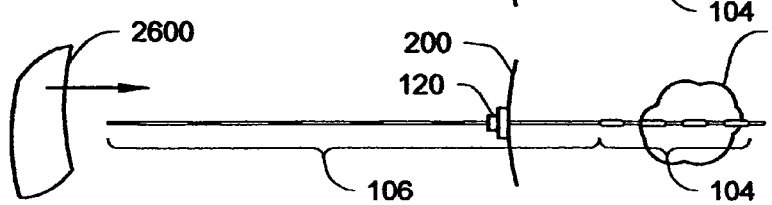
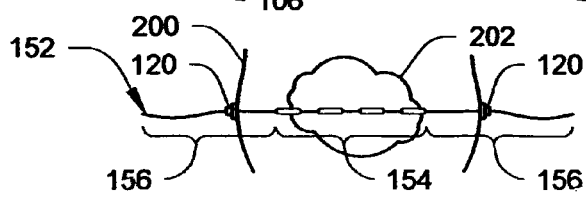

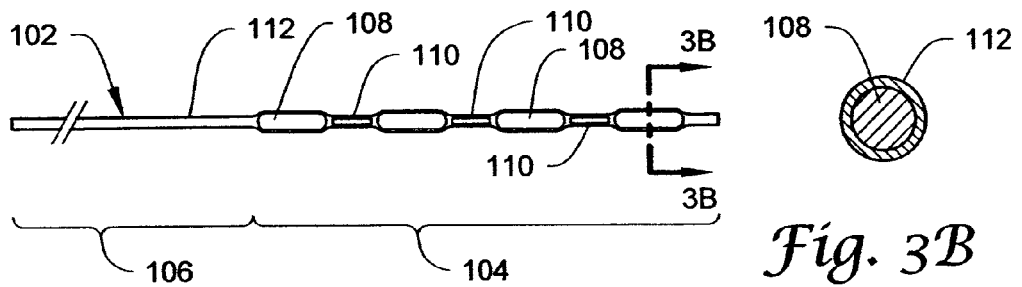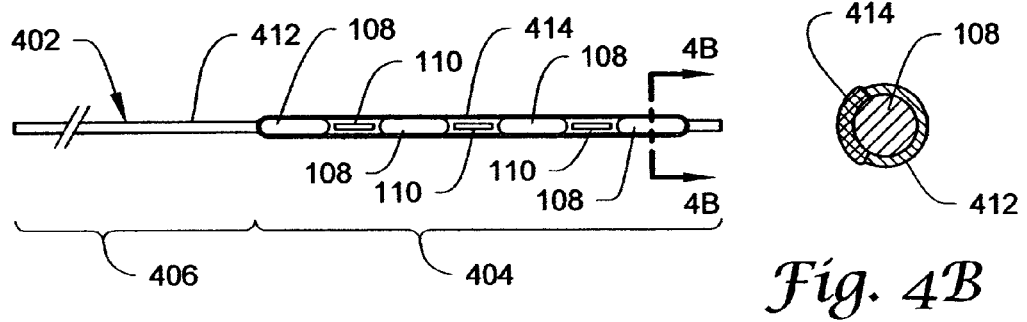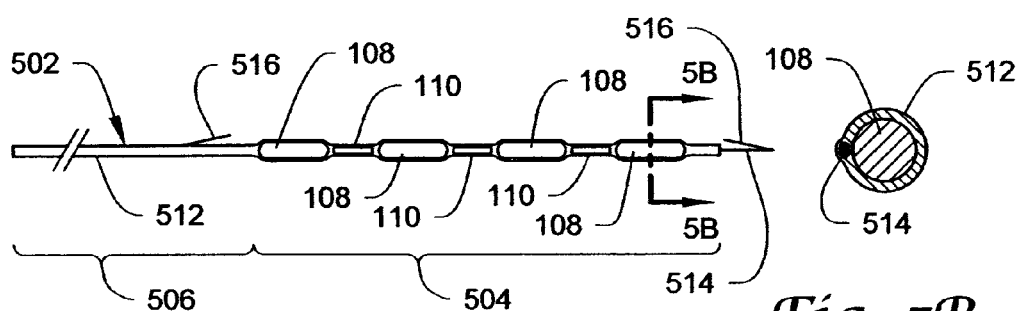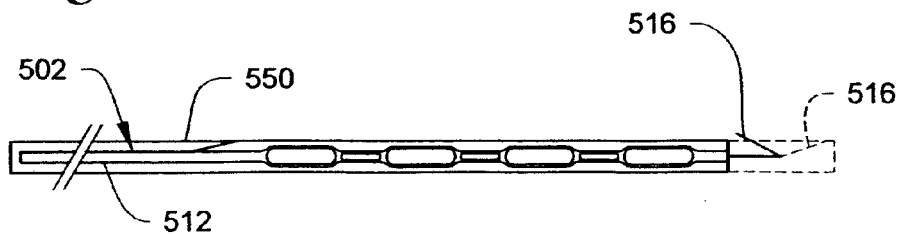

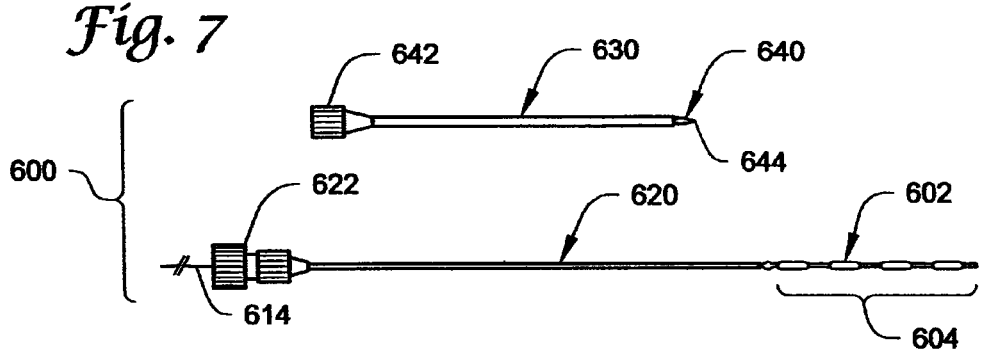
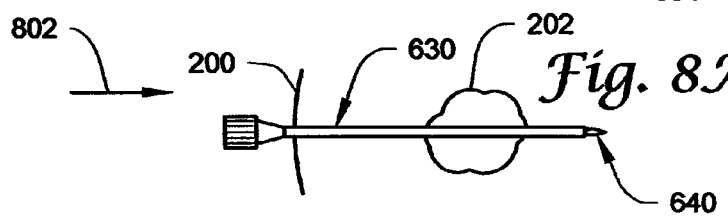
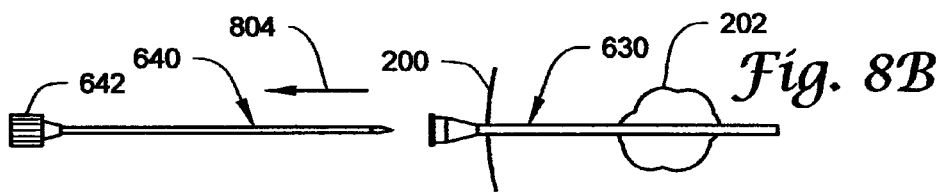
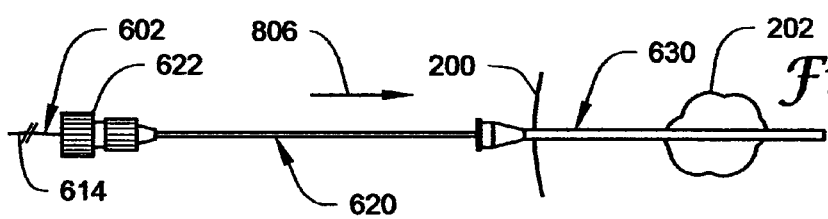
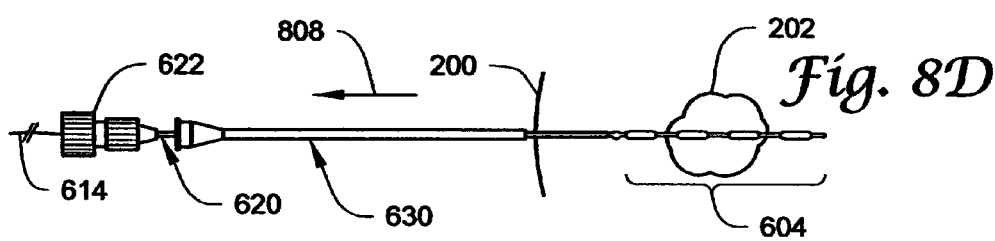
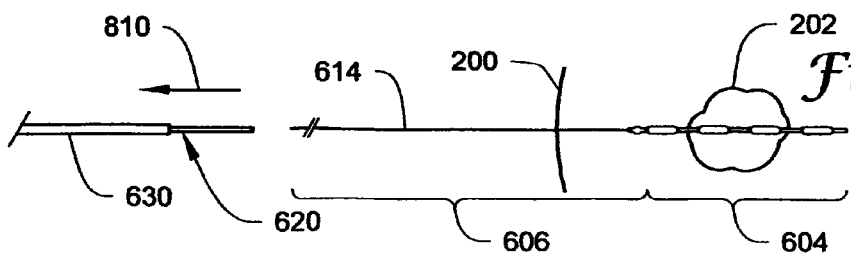

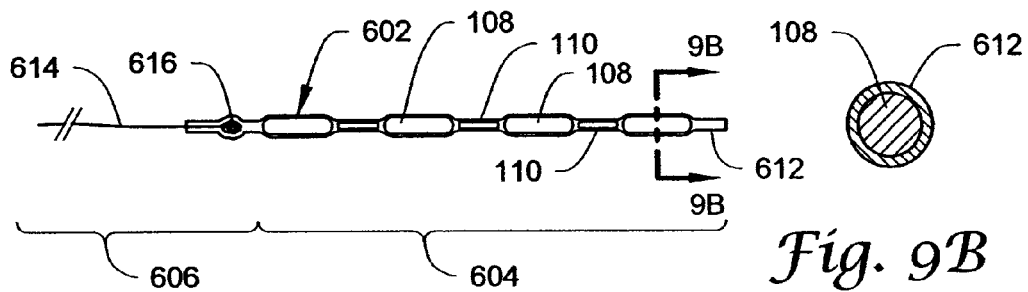
Fig. 9A
Fig. 9B
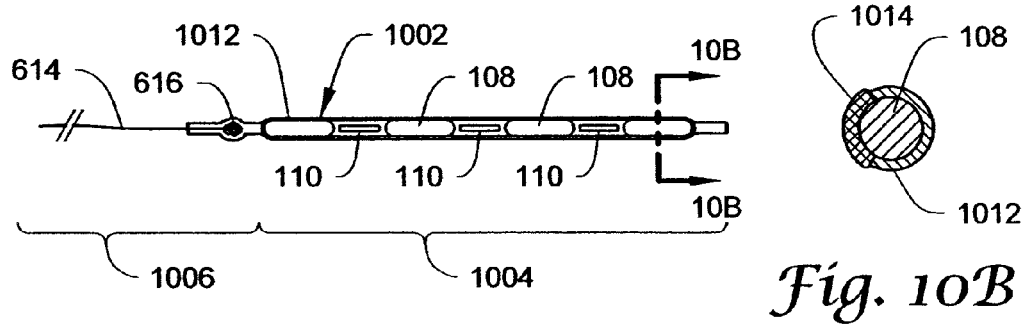
Fig. 10A
Fig. 10B
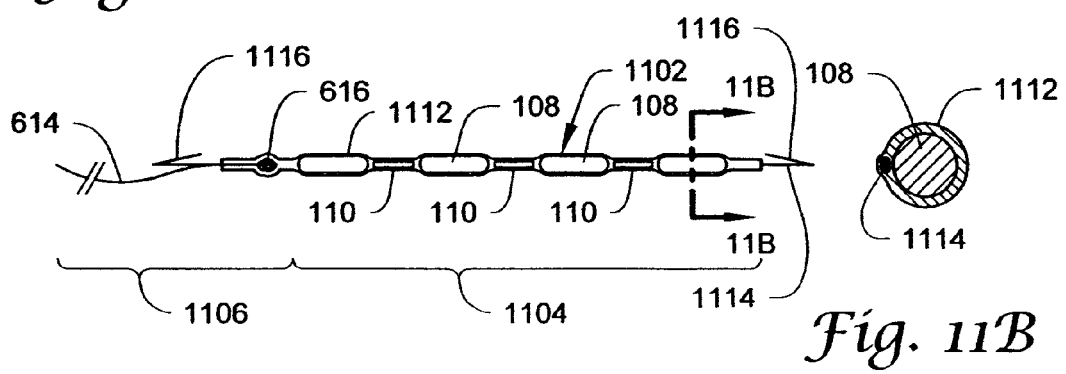
Fig. 11A
Fig. 11B

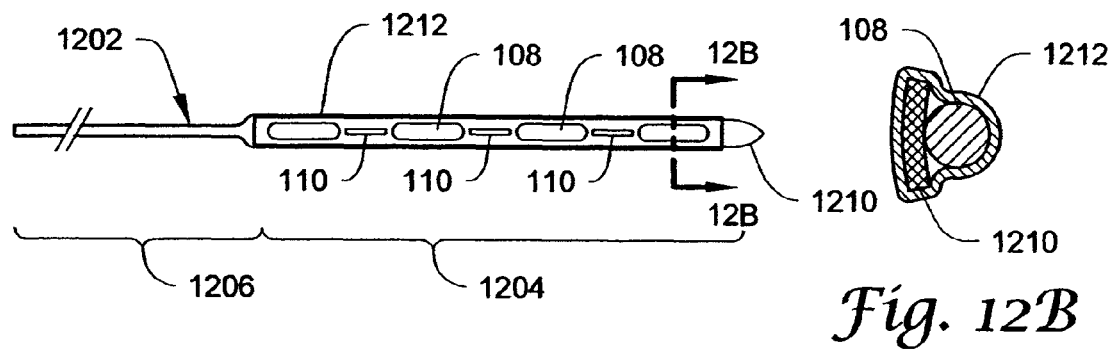
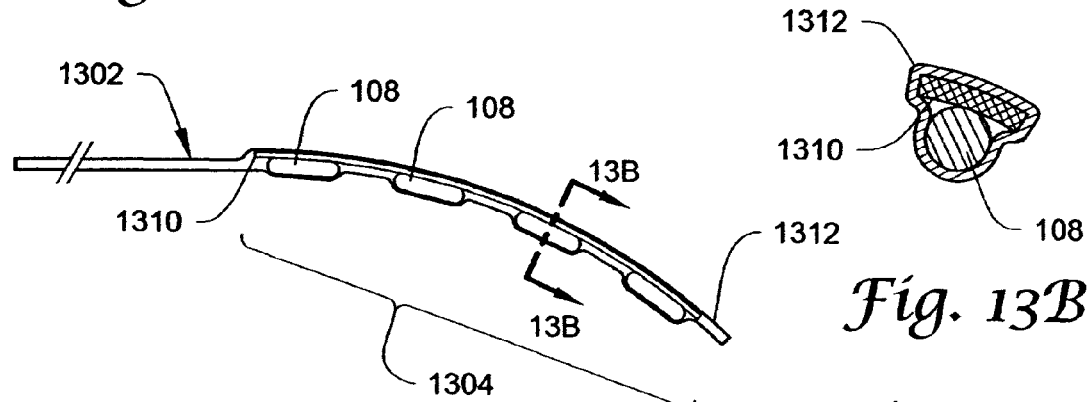
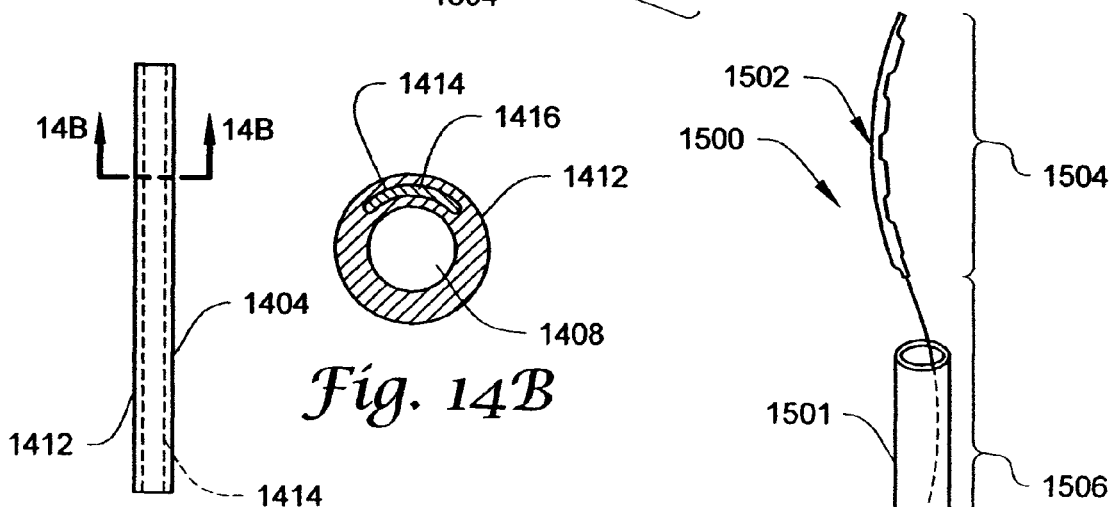
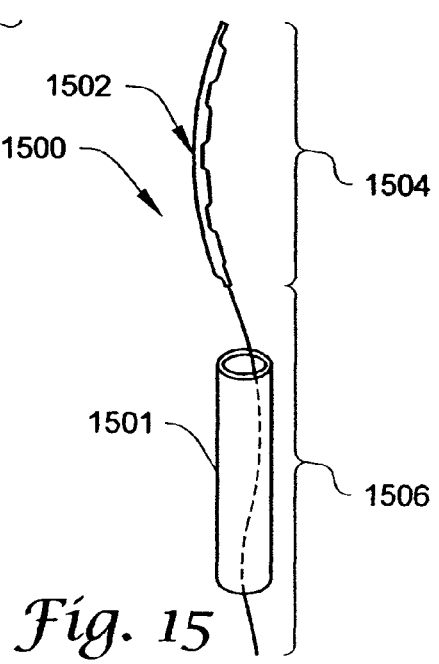

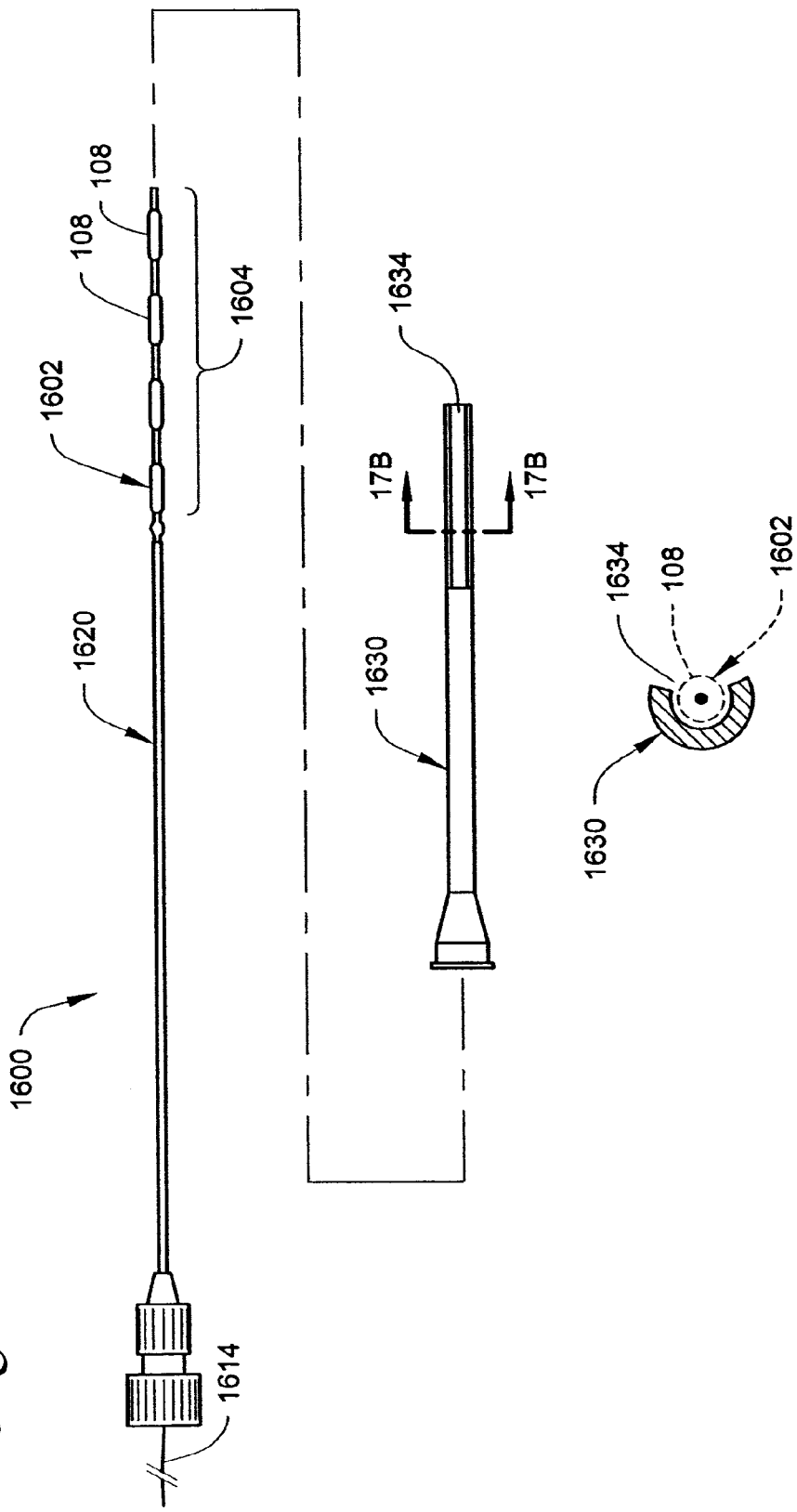

ent of the needles 65
BRACHYTHERAPY APPARATUS AND METHODS FOR USING SAME

RELATED APPLICATIONS

This application is a continuation of co-pending application Ser. No. 10/658,518, filed Sep. 9, 2003, which claims the benefit of U.S. Provisional Application No. 60/409,449, filed 10 Sep. 2002, which is hereby incorporated herein by reference in its entirety.

TECHNICAL FIELD

The invention pertains generally to medical treatment and, more specifically, to apparatus, methods, and systems for providing brachytherapy to a human or other mammalian body.

BACKGROUND

Brachytherapy is a type of radiation therapy used to treat malignant tumors such as cancer of the breast or prostate. In general, brachytherapy involves the positioning of a radiation source directly into target tissue, which may typically include the tumor and/or surrounding tissue that may contain potentially cancerous cells (such as a cavity or void created by removal of the tumor).

Brachytherapy is often divided into two categories: high dose rate (HDR); and low dose rate (LDR). In HDR brachytherapy, a high activity radiation source is placed into the target tissue, often via a previously implanted catheter, for a short period of time, e.g., seconds to a few minutes. In contrast, LDR brachytherapy places a low activity radiation source into the tumor for a longer, e.g., indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to the target tissue, e.g., the tumor, gland, or other surrounding tissue. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Moreover, for patients, the relatively longer implantation period associated with LDR brachytherapy may result in fewer visits to a healthcare facility over the course of radiation treatment.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they are, in common applications (e.g., prostate brachytherapy), provided in cylindrically shaped capsules that are approximately the size of a grain of rice, e.g., about 0.8 millimeters (mm) in diameter and about 4.5 mm in length, and are often referred to as "seeds.:

LDR seeds are often delivered through needles using a guide template. The guide template may include a matrix of holes that guide the longitudinal advancement of the needles to insure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, the LDR seeds are typically left indwelling and free floating within the target tissue and are, therefore, susceptible to migration. Moreover, once implanted, LDR seeds are generally not considered to be removable or repositionable. LDR brachytherapy may also require careful dose distribution calculations and seed mapping prior to, and often during, seed implantation. Such calculation and mapping allows effective radiation delivery to the target tissue volume, while minimizing radiation to surrounding healthy tissue (the urethra and rectum, for example, in prostate brachytherapy). Yet, while such dose calculation and seed mapping techniques are effective, problems—such as potentially significant variability in accuracy of seed placement among different clinicians—may exist.

Yet another issue with conventional LDR brachytherapy techniques is that many of these techniques often require the radioactive seeds to be manipulated individually at the time of implantation, an often time-consuming process. Moreover, conventional LDR delivery needles are generally limited to delivering the seeds linearly (along a relatively straight line). Thus, to achieve the desired therapy profile, numerous implants (e.g., about 50-100 seeds are common with prostate brachytherapy), in conjunction with potentially complex dose distribution and mapping techniques and equipment, are often required.

SUMMARY

The present invention is broadly directed to apparatus and methods for delivering brachytherapy to a localized target tissue region. While the invention is useful in treating most any area of the body, it offers particular advantages in the treatment of breast tissue, e.g., breast tumors or lumpectomy cavities. For example, the invention may be used to place and remove a localized radiation source for both neoadjuvant and post-excisional treatment.

In one embodiment, a flexible implantable brachytherapy treatment device is provided. The device may include one or more of: a therapy delivery portion including a non-dissolving casing; and one or more radiation sources fixed relative to the casing. In other embodiments, an elongate removal portion extending from the therapy delivery portion may be provided.

In another embodiment, a brachytherapy treatment device operable for both implantation into, and subsequent removal from, a target tissue region of a body is provided. The device may include a therapy delivery portion having one or more radioactive sources fixed relative to a casing, where the casing is operable to be positioned in direct contact with the target tissue region. The device may also include at least one non-dissolving flexible tail portion extending from the therapy delivery portion.

In yet another embodiment, a brachytherapy treatment device for implanting a plurality of radioactive sources into a target tissue region of a body, and for removing multiple radioactive sources at the completion of brachytherapy, is provided. The device may include a therapy delivery portion having a heat-shrinkable casing operable to securely retain the multiple radioactive sources. The device may further include a non-dissolving, first flexible tail portion extending from a first end of the therapy delivery portion, and a non-dissolving, second flexible tail portion extending from a second end of the therapy delivery portion.

In still yet another embodiment, a device for delivering brachytherapy to a target tissue region of a body is provided wherein the device may include an elongate, non-dissolving flexible casing adapted to securely hold therein a plurality of radioactive sources.

In yet another embodiment, a device for delivering brachytherapy to a lesion of the breast is provided, wherein the device includes a non-dissolving flexible casing adapted to securely hold therein a radioactive source.

In still another embodiment, a brachytherapy delivery apparatus is provided. The apparatus may include means for simultaneously implanting, in a parallel array, a plurality of catheters into a target tissue region, wherein each catheter of the plurality of catheters is operable to receive one or more radioactive sources.

In still another embodiment, a garment for attenuating radiation from an implantable brachytherapy device is provided. The garment includes a fabric portion operable to cover an area surrounding the brachytherapy device, and a radiation attenuating material associated with the fabric portion.

In still yet another embodiment of the invention, a kit for delivering brachytherapy to a target tissue region of a body is provided. The kit may include a removably implantable elongate brachytherapy device having: a therapy delivery portion; one or more radioactive sources secured to the therapy delivery portion; and at least one non-dissolving flexible tail portion extending from the therapy delivery portion. A catheter for delivering the brachytherapy device to the target tissue region may also be provided.

Another embodiment of the invention provides a catheter for implanting at least one radioactive source into a target tissue region of a body. The catheter may have a radiotransparent portion and a radioabsorptive portion, wherein the radioabsorptive portion extends substantially along a longitudinal length of a dose delivery portion of the catheter.

In still another embodiment, a catheter assembly for delivering one or more radioactive sources to a target tissue region of a body is provided. The catheter assembly may include a first catheter member and a second catheter member positionable within the first catheter member. The second catheter member may be operable to extend outwardly from an opening at or near a distal end of the first catheter member such that an axis of the second catheter member intersects an axis of the first catheter member.

In another embodiment, a catheter assembly for delivering a high dose radiation (HDR) source to a target tissue region of a body is provided. The catheter assembly may include a catheter shaft comprising a distal end and a proximal end, and an inflatable balloon coupled to the catheter shaft between the distal end and the proximal end. A dose delivery lumen may be provided and extend along the catheter shaft between the proximal end and the distal end. A dose delivery portion of the catheter shaft surrounded by the inflatable balloon may include a radioabsorptive portion.

In still yet another embodiment, a system for implanting a plurality of brachytherapy devices into a target tissue region of a body is provided. The system may include a catheter guiding template, a cartridge receiver associated with the catheter guiding template, and a pre-assembled cartridge having a plurality of delivery catheters arranged in a fixed relationship. The cartridge receiver is operable to receive the pre-assembled cartridge.

Yet another embodiment addresses a method of providing brachytherapy to a target tissue region of a body. The method may include providing an elongate brachytherapy device having: a therapy delivery portion with one or more radioactive sources secured thereto; and a non-dissolving flexible tail portion extending from the therapy delivery portion. The therapy delivery portion may be located at a static position within the target tissue region, wherein the flexible tail portion protrudes outside the body. Brachytherapy may be delivered with the one or more radioactive sources.

In still another embodiment, a method of providing brachytherapy to a target tissue region of a body is provided. The method may include simultaneously advancing multiple catheters into a target tissue region, and delivering one or more radiation sources through at least one catheter of the multiple catheters.

In still yet another embodiment, a method of providing brachytherapy to a target tissue region of a body is provided. The method may include simultaneously advancing multiple catheters into a target tissue region, and delivering one or more radiation sources through at least one catheter of the multiple catheters.

In yet another embodiment, a method for delivering brachytherapy to a lesion of the breast is provided. The method may include implanting a radioactive source at or near the lesion, delivering brachytherapy, and removing the lesion. The radioactive source may be removed prior to or during removal of the lesion.

The above summary of the invention is not intended to describe each embodiment or every implementation of the present invention. Rather, a more complete understanding of the invention will become apparent and appreciated by reference to the following detailed description and claims in view of the accompanying drawing.

BRIEF DESCRIPTION OF THE VIEWS OF THE DRAWINGS

The present invention will be further described with reference to the drawing, wherein:

FIG. 1 illustrates an exemplary brachytherapy apparatus or kit in accordance with one embodiment of the invention;

FIGS. 2A-2E are diagrammatic illustrations of a method of using the brachytherapy apparatus of FIG. 1;

FIG. 2F is a diagrammatic illustration of another brachytherapy apparatus in accordance with the present invention;

FIGS. 3A-3B are enlarged partial views of a brachytherapy device in accordance with one embodiment of the invention;

FIGS. 4A-4B are enlarged partial views of a brachytherapy device in accordance with another embodiment of the invention;

FIGS. 5A-5B are enlarged partial views of a brachytherapy device in accordance with yet another embodiment of the invention;

FIG. 5C is a view of the brachytherapy device of FIGS. 5A-5B illustrating an exemplary removal method;

FIG. 7 illustrates the brachytherapy apparatus of FIG. 6 as it may be partially assembled;

FIGS. 8A-8E are diagrammatic illustrations of a method of using the brachytherapy apparatus of FIGS. 6 and 7;

FIGS. 9A-9B are enlarged partial views of a brachytherapy device in accordance with another embodiment of the invention;

FIGS. 10A-10B are enlarged partial views of a brachytherapy device in accordance with yet another embodiment of the invention;

FIGS. 11A-11B are enlarged partial views of a brachytherapy device in accordance with still yet another embodiment of the invention;

FIGS. 12A-12B are enlarged partial views of a brachytherapy device in accordance with still another embodiment of the invention;

FIGS. 13A-13B are enlarged partial views of a brachytherapy device in accordance with yet another embodiment of the invention;

FIGS. 14A-14B are enlarged partial views of a brachytherapy device in accordance with still yet another embodiment of the invention;

FIG. 15 is a diagrammatic view of a brachytherapy apparatus in accordance with another embodiment of the invention;

FIGS. 16A-16E illustrate a dual, off-axis catheter assembly; and FIGS. 16F-16G illustrate a spiral-shaped catheter;

FIGS. 17A-17B illustrate a brachytherapy apparatus in accordance with yet another embodiment of the invention;

DETAILED DESCRIPTION OF EXEMPLARY EMBODIMENTS

Figure 6:
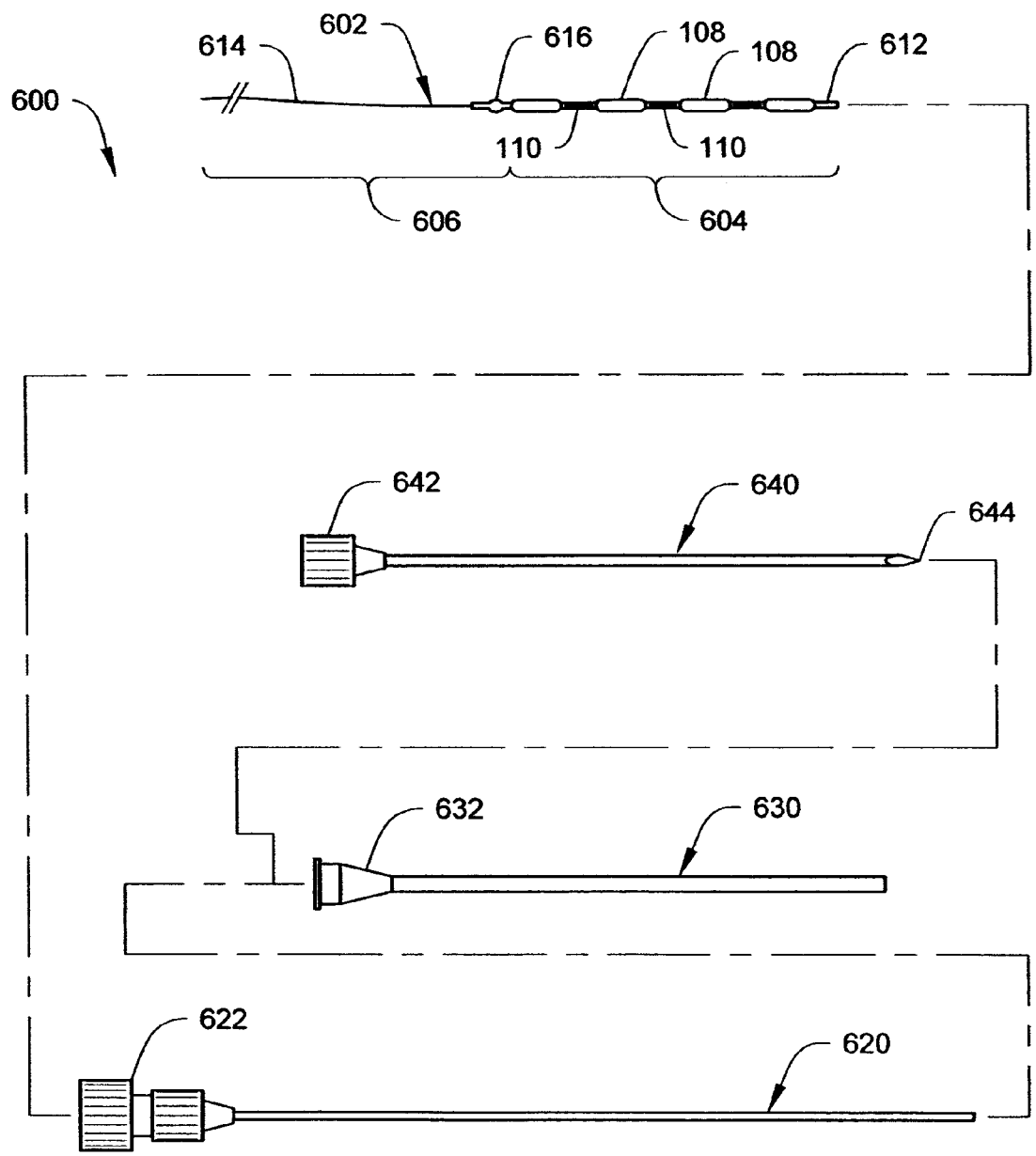
FIG. 6 is an exploded view of a brachytherapy apparatus or kit in accordance with yet another embodiment of the invention.

In the following detailed description of exemplary embodiments, reference is made to the accompanying figures of the drawing which form a part hereof, and in which are shown by way of illustration specific embodiments in which the invention may be practiced. It is to be understood that other embodiments may be utilized and structural changes may be made without departing from the scope of the present invention.

Generally speaking, the present invention is directed to brachytherapy apparatus and methods. More particularly, the present invention provides a system for delivering one or more therapeutic elements (e.g., radiation sources) relative to a target tissue region. Once delivered, the radiation sources may be either immediately withdrawn (e.g., in HDR applications), or left in place, e.g., implanted, for a defined period (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. Unlike conventional LDR brachytherapy, apparatus and methods of the present invention provide not only indwelling therapy using pre-arranged packages of radioactive sources, e.g., seeds, but also allow easy removal of the radiation sources at the completion of brachytherapy.

As used herein, "radiation source" may include most any therapeutic element operable to deliver a dose of radiation. For example, the radiation source may be a radioactive seed or, alternatively, a LDR or HDR wire element (e.g., Iridium wire).

The term "implantable," as used herein, indicates the capability of a device to be inserted into the body and then maintained in a fixed or static position, relative to the immediately surrounding tissue, for an extended period of time, e.g., an hour or more and, more preferably, several hours or more.

Furthermore, "target tissue," "target tissue region," and "target tissue volume," as used herein, may include most any portion of a human (or other mammalian) body that has been identified to benefit from radiation therapy. For example, the target tissue region may be a tumor or lesion itself, tissue proximate or surrounding the tumor, or a cavity created by tumor excision (such as the surrounding tissue associated with a lumpectomy cavity of the breast).

It should be noted that, while described herein primarily with respect to LDR brachytherapy, the apparatus and methods of the present invention may also have application to HDR brachytherapy (e.g., HDR catheters) as further described below. Moreover, while described herein with respect to brachytherapy, the present invention may have application to other therapy regimens that benefit from the removable implantation of therapy-delivering elements.

For the sake of brevity, the invention is described herein as it relates to the treatment of breast cancer. However, this particular application is not limiting. That is, those of skill in the art will readily appreciate that the systems, apparatus, and methods described herein may find application to most any cancer that may receive benefit from brachytherapy.

With this introduction, attention is now directed to the figures of the drawing. FIG. 1 illustrates an exemplary kit or apparatus 100 for providing brachytherapy to a target tissue region of a body. The apparatus 100 may include an elongate and flexible, removably implantable brachytherapy treatment device 102 (also referred to as hereinafter as "brachytherapy device 102") having a therapy delivery portion 104, and an elongate and flexible tail portion 106. The tail portion 106 may, as further described below, provide the ability to remove the device 102 at therapy completion. Other components described below, e.g., locking members, may also be included with the apparatus 100.

The term "flexible" is used herein to describe a component that is highly pliant, e.g., a component that may be substantially and easily bent, flexed, and/or twisted without experiencing breakage or permanent deformation.

The therapy delivery portion 104 may form a carrier pod of therapeutic elements, e.g., radiation sources such as radioactive seeds 108, secured relative to one another and to the therapy delivery portion 104. One or more spacers 110 may optionally be located between each seed 108 to obtain the desired seed separation.

The seeds 108 may be produced from most any acceptable radioactive source now known (e.g., radioactive Palladium or Iodine) or later developed. Typically, numerous seeds 108 are provided and precisely placed along the length of the therapy delivery portion 104 in order to correspond to the desired therapy delivery regimen. While the radioactive sources are described herein as seeds 108, they may take other forms such as a continuous filament (or numerous discontinuous segments) of radioactive wire (e.g., Iridium wire).

In some embodiments, the brachytherapy device 102 may include a flexible casing or casing member, illustrated in the figures as tube or tube member 112, in which the seeds 108 and optional spacers 110 are securely retained. In some embodiments, the casing is made from a non-dissolving and flexible, heat-shrinkable tubing material. "Heat-shrinkable tubing," as used herein, refers to tubing, such as various plastic tubing, in which subsequent thermal exposure causes the tubing to shrink, thereby allowing it to securely retain the seeds 108 in place. Exemplary heat-shrinkable materials include polyester, fluorinated polymers, and polyolefins.

While most any number of tubing sizes are contemplated, in one embodiment, the tube 112 may have an initial inside diameter of about 1 mm and a wall thickness of about 0.05 mm. Once heated, the tube 112 may shrink (if unconstrained) to an outer diameter ranging from about 0.3 mm to about 0.6 mm.

While the casing is described herein generally as tube-shaped, the casing may, in other embodiments, be most any shape that is capable of effectively securing the individual seeds 108 relative to the casing and to one another.

Once the seeds 108 and optional spacers 110 are located within the tube 112, the tube may be shrunk by exposure to heat, thus contracting the tube 112 around the seeds 108. The tail portion 106 may be formed by an integral portion, e.g., extension, of the casing (tube 112) that extends beyond the seeds 108. To reduce the diameter of the tail portion 106, it may also be thermally treated (shrunk). Other embodiments (described below) may utilize a two-part brachytherapy device, e.g., a separate filament tail portion attached to the therapy delivery portion.

Regardless of the specific configuration, the brachytherapy devices 102 described herein provide not only proper spacing of the seeds 108, but also facilitate subsequent seed identification and removal. Moreover, because the seeds are contained within the pod defined by the therapy delivery portion 104, seeds may not require individual handling, thus simplifying inventory and handling prior to, and at the time of, implantation.

The components of the device 102, including the casing (tube 112) and tail portion 106, are preferably constructed of non-dissolving materials. The term "non-dissolving" is used herein to indicate most any material that does not substantially deteriorate or otherwise break down during the implantation period.

The brachytherapy apparatus 100 may also include a catheter, e.g., needle 114. While illustrated as needle 114, any other type of catheter, such as the cannulae described further below, may also be used without departing from the scope of the invention. The needle 114 defines a lumen 115 of sufficient size to allow the therapy device 102 to pass through as indicated in FIG. 1. The needle 114, in some embodiments, may further include a hub 116 at a proximal end to assist with manipulation of the needle and insertion of the therapy device 102. A distal end of the needle 114 may form a sharpened tip 117 operable to pierce the body as further described below. The needle 114 may be made from most any suitable biocompatible material. For example, it may be made from metal, e.g., stainless steel, titanium, or nickel titanium alloy. It may also include a removable outer sheath (not shown) made of plastic, e.g., fluorinated polymers.

FIGS. 2A-2E illustrate an exemplary method of using the brachytherapy apparatus 100 of FIG. 1. Once a target tissue region 202 (a tumor or tumor cavity) within body 200 is accurately located, the needle 114 may be inserted into the body 200, as shown by arrow 203 in FIG. 2A, to a predetermined depth. The relative location(s) of the needle 114 and/or the target tissue region 202 may be determined by most any method, e.g., via ultrasound, CT scan, stereotactic X-ray, etc. The needle 114 may further be aligned with the use of a needle guiding template as further described below, or by other techniques.

Next, the brachytherapy device 102 may be inserted into the lumen 115 of the needle 114, as shown by arrow 205 in FIG. 213, until the therapy delivery portion 104 is located at the desired depth relative to the target tissue region 202 as shown in FIG. 2C. To assist in determining the approximate insertion depth of the therapy device 102, the tail portion 106 may include measurement demarcations 118. Other location verification techniques, e.g., X-ray, ultrasound, etc., may also be used.

Once the therapy device 102 is located at the desired depth, the needle 114 may be withdrawn from the body in the direction 207 as shown in FIG. 2D, leaving the therapy delivery portion 104 of the device 102 at the desired position within the body 200. The tail portion 106 is preferably of sufficient length such that it extends outside of the body 200 as shown in FIG. 2E. That is, the tail portion 106 may extend externally through a puncture made by the needle 114.

Figure 27:
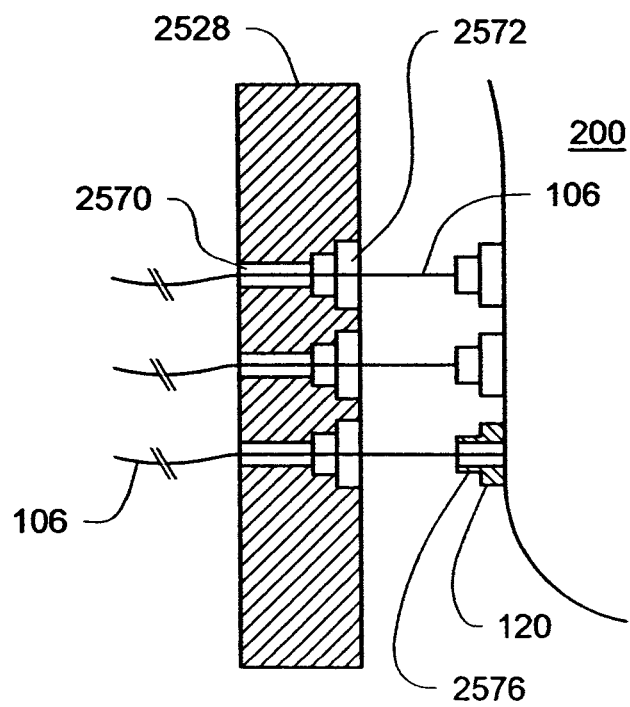
FIG. 27 is a cross-section of a portion of the delivery system of FIGS. 25A-25D.

In order to prevent migration of the therapy delivery portion 104, a locking member 120 may be crimped or otherwise attached to the tail portion 106 of the therapy delivery device 102 immediately adjacent the associated puncture in the body 200. The locking member 120 may assist in maintaining the location of the therapy delivery portion 104 relative to the target tissue region 202. While most any locking member may be used, one embodiment utilizes a malleable, hat- or U-shaped lock that can be easily and securely crimped to the tail portion with, for example, a surgical clip applier or similar tool. An enlarged view of an exemplary locking member is illustrated in FIG. 27.

For illustration purposes, only a single therapy delivery device 102 is shown in FIGS. 2A-2E. However, in practice, multiple devices would be utilized to provide adequate dosage to the target tissue region 202. The actual number of devices 102 may vary depending on various parameters such as lesion size, radiation source activity levels, and proximity to other organs/vulnerable tissue (e.g., skin, chest wall). However, quantities ranging from about 5 to about 25 devices are contemplated.

FIG. 2F illustrates a variation of the therapy device 102 of FIGS. 2A-2E that may offer additional benefits, especially to the treatment of breast cancers. In this embodiment, a therapy device 152 similar in most respects to the device 102 is provided. However, the device 152 may include both a first tail portion extending from a first end of a therapy delivery portion 154 and a second tail portion extending from a second end, i.e., it may include a tail portion 156 at each end of the therapy delivery portion 154. During implantation, the needle 114 may pass completely through the body, e.g., breast 200, such that one tail portion 156 extends out the opposite side of the breast 200. In this way, locking members 120 may be secured at two locations relative to the target tissue region 202, thus preventing or substantially limiting movement of the therapy delivery portion 154 relative to the target tissue region 202.

Unlike conventional brachytherapy catheters, which may be 2 mm or more in diameter, the devices of the present invention, e.g., devices 102, may be about 1 mm or less in diameter at the therapy delivery portion 104 and even smaller at the tail portion 106. This construction permits the devices 102 to be relatively small and flexible, and thus less obtrusive to the patient. In fact, the size and flexibility of the tail portions 106 may be similar to that of a conventional suture. As a result, securing the tail portions 106 may be accomplished in any number of ways including, for example, folding the tail portions against the contour of the surrounding body and fixing them such as by tying the ends and/or securing the ends with adhesive, the latter represented by bandage 2600 in FIGS. 2E and 26.

FIG. 3A is an enlarged view of the therapy device 102 of FIG. 1. As clearly illustrated in this view, the therapy device 102 may include the therapy delivery portion 104 and the tail portion 106. As described above, the therapy delivery portion 104 may include one, or preferably more, radioactive seeds 108 separated by spacers 110 and encased within the casing, e.g., heat-shrinkable tube 112. The tail portion 106 may be formed by the portion of the tube 112 that does not surround the seeds 108. In some embodiments, the conformal properties of the tube 112 may be sufficient to ensure proper seed spacing, thus negating the need for spacers 110. FIG. 3B illustrates a section view through a seed 108 and the tube 112 taken along line 3B-3B of FIG. 3A.

FIGS. 4A-4B illustrate a therapy device 402 in accordance with another embodiment of the present invention. The device 402 is similar in many respects to the device 102 described above. For example, the device 402 may include a therapy delivery portion 404 and a tail portion 406 as illustrated in FIG. 4A. A casing, e.g., heat shrinkable tube 412, may be used to encase the seeds 108 and optional spacers 110 as well as to form the tail portion 406. However, unlike the embodiment of FIGS. 3A-3B, the tube 412 may include a radioabsorptive portion 414, e.g., a substance or liner, positioned along a portion of the circumference of the therapy delivery portion 404 (see FIG. 4B). The radioabsorptive portion 414 may include a radiation attenuating material, and thus reduce radiation exposure to tissue blocked by the radioabsorptive portion 414 as opposed to tissue not blocked by the portion 414. While not limited to any particular embodiment, the radioabsorptive portion may be formed by a substance (e.g., Tungsten, Nickel-Titanium alloy, stainless steel) applied to, or impregnated within, a portion of the tube 412. Alternatively, the radioabsorptive portion(s) may be formed by a liner within, or secured to a portion of, the tube 412. FIG. 4B illustrates a section view through a seed 108 and the tube 412 taken along line 4B-4B of FIG. 4A.

The term "radiotransparent" is used herein to indicate only that the identified portion of the apparatus or device is relatively more transparent to radiation than the portion identified as "radioabsorptive."

FIGS. 5A-5B illustrate a therapy device 502 in accordance with yet another embodiment of the present invention. The device 502 is similar in many respects to the device 102 described above. For example, the device 502 may include a therapy delivery portion 504 and a tail portion 506 as shown in FIG. 5A. A casing, e.g., heat shrinkable tube 512, may be used to encase the seeds 108 and optional spacers 110 as well as to form the tail portion 506. However, unlike the previous embodiments, the therapy device 502 may incorporate an anchor member, e.g., a flat or round cross-section anchor wire 514, which extends along at least a part of the therapy delivery portion 504. The anchor wire 514 protrudes from one or both ends of the therapy delivery portion and may be bent to form one or more hooks or anchors 516.

When the therapy delivery portion 504 exits the needle 114 (see FIG. 1) during implantation, the anchors 516 may extend and engage surrounding tissue, thereby assisting in preventing migration of the therapy device 502. While only a single anchor is shown at each end of the therapy delivery portion 504, other embodiments may include multiple anchors at one or both ends to further resist movement, e.g., rotating or twisting. FIG. 5B illustrates a section view through a seed 108 and the tube 512 taken along line 5B-5B of FIG. 5A.

After the desired dose of radiation has been delivered, the therapy device 102 (or any of the other therapy devices described herein, e.g., devices 402 or 502), may be removed in any number of ways. For example, the device 102 may be removed by first removing any dressing (e.g., bandage 2600 of FIG. 2E) and locking member(s) 120, and then simply applying a pulling force to one of the tail portions 106 that extends outside of the body 200. Alternatively, the devices 102 may be removed prior to or during excisional surgery of the tumor 202 via known methods, e.g., via methods similar to excision utilizing localization wires.

Where the therapy device 102 includes internal retaining elements, e.g., anchors 516 of device 502 (FIG. 5A), a removal catheter 550 as shown in FIG. 5C may be used. The removal catheter 550 is similar in most respects to the delivery cannulae and needles described herein, e.g., needle 114. The catheter 550 may be threaded over the tail portion 106 and advanced until it encompasses the therapy delivery portion 104. For example, the removal catheter 550 may be advanced until its distal end engages the distal retaining element(s), e.g., distal anchor 516 of FIG. 5A. Further advancement of the removal catheter 550 may bend the anchor sufficiently to permit the therapy delivery portion to slide into the removal catheter as shown in the broken line representation of FIG. 5C. The device 502 and the removal catheter 550 may then be withdrawn as a unit from the body.

With any of the methods described herein, the time that the brachytherapy devices remain implanted may vary according to the desired therapy regimen. While not wishing to be bound to any fixed period, implantations from about one hour up to about eight weeks or more are contemplated for therapy. However, for breast brachytherapy, implantation periods ranging from about one day to several weeks are more likely. Moreover, because of the construction of the devices, e.g., devices 102, they may be removed over a range of timeframes subsequent to implantation. This is in contrast to the permanent placement associated with conventional LDR brachytherapy and the short exposure time associated with conventional HDR brachytherapy. As a result, intermediate activity radiation sources may be utilized with the methods and apparatus of the present invention, as well as conventional low and, as further described below, high activity sources.

FIG. 6 illustrates a brachytherapy kit or apparatus 600 in accordance with another embodiment of the invention. Unlike the apparatus 100 of FIG. 1, the apparatus 600 may include, among other components, at least a removably implantable brachytherapy treatment device (brachytherapy device 602), a pusher or pusher member 620, a catheter, e.g., cannula or cannula member 630, and a sharp obturator 640.

The therapy device 602, once again, may include a therapy delivery portion 604 and a removal or tail portion 606. The therapy delivery portion 604 may include one or more seeds 108 and optional spacers 110. The seeds 108 may be enclosed within a casing, e.g., heat-shrinkable tube or tube member 612, similar in most respects to the tube 112 described above.

The tail portion 606 in this embodiment, however, is formed by an elongate filament or wire, e.g., a non-dissolving surgical suture 614, coupled or otherwise attached to the therapy delivery portion 604. While most any method of attaching the suture 614 to the therapy delivery portion 604 is possible, one embodiment forms a knot 616 in the suture. The knot 616 may be captured when the tube 612 is heat-shrunk to the therapy delivery portion 604. In other embodiments, the suture 614 may be knotted around or otherwise attached directly to the therapy delivery portion 604. Such suture attachment methods are exemplary only, however, as most any other method of attaching the suture 614 to the therapy delivery portion 604 is possible. The suture 614, as with the tail portion 106 described above, is preferably made from a non-dissolving material, e.g., polypropylene, polyester, polyamide.

The pusher member 620 may include a lumen through which the therapy device 602 may pass as indicated in FIGS. 6 and 7. The pusher member may include a suture locking device 622, e.g., a luer hub, at a proximal end to assist with loading and securing of the therapy device 602. The locking device 622 may secure the suture 614 relative to the pusher 620 as further described below. While illustrated as a luer hub, the locking device 622 may include most any friction or clamping device known in the art. For example, the locking device may be an O-ring that may be selectively compressed to pinch the suture 614.

The cannula member 630 may also include a lumen through which the pusher member 620 may pass as indicated in FIG. 6. The cannula member 630 may include a luer hub 632 at its proximal end that is operable to secure the cannula member relative to the either the sharp obturator 640 or the pusher member 620 when either is slid into the lumen of the cannula member as further described below.

The sharp obturator 640 may include a handle portion with a hub 642 at a proximal end, and a sharp point 644 operable to pierce body tissue at its distal end. The handle portion may permit comfortable manipulation of the obturator 640. The external diameter of the obturator 640 may be sized so that it fits within the lumen of the cannula member 630 as indicated in FIG. 6.

The components of the apparatus 600 may be made from most any suitable biocompatible material. For example, the cannula member 630, the pusher member 620, and the sharp obturator 640 may be made from metal, e.g., stainless steel or Titanium, or plastic.

FIG. 7 illustrates the apparatus 600 as it may be assembled prior to use. The sharp obturator 640 may be placed into the cannula 630 such that the sharp distal end 644 of the obturator protrudes from the distal end of the cannula 630 as illustrated. The therapy device 602, which includes the therapy delivery portion 604 and the suture 614 as described above, may be positioned within the pusher member 620 such that the therapy delivery portion 604 extends from its distal end and the suture 614 extends from the hub 622 at its proximal end. The suture 614 may be pulled from the proximal end of the pusher member 620 until the therapy delivery portion 604 is at or near the distal end of the pusher member 620 as shown. The locking device 622 may then be engaged to hold the suture 614, and thus the therapy delivery portion 604, in place relative to the pusher member 620.

FIGS. 8A-8E illustrate an exemplary method of using the system 600 for delivery of brachytherapy to a portion of a body, e.g., breast 200. Once the target tissue region 202, e.g., tumor or tumor cavity, is identified, the combined cannula 630 and sharp obturator 640 (see FIG. 7) may be advanced into the target tissue region 202 as illustrated by arrow 802 in FIG. 8A. When the distal end of the cannula 630 reaches the desired depth, the sharp obturator 640 may be removed (moved in the direction 804) through the proximal end of the cannula as shown in FIG. 8B, while leaving the cannula 630 in place.

The combined pusher member 620 and therapy device 602 (see FIG. 7) may then be inserted into the proximal end of the cannula 630, in the direction 806, as shown in FIG. 8C. The pusher 620, and therapy device 602, may be inserted until the therapy portion 604 is at its desired location, e.g., at or near the distal end of the cannula 630. Location of the therapy portion 604 may be assisted by image guidance, e.g., stereotactic X-ray, ultrasound, CT, etc.

Once the therapy portion 604 is positioned, the cannula 630 may be retracted (moved in the direction 808), exposing the therapy portion 604 to the target tissue region 202 as shown in FIG. 8D. The locking device 622 may then be unlocked such that the pusher member 620 and cannula 630 may be fully withdrawn (moved in the direction 810) from the body 200 as shown in FIG. 8E. The therapy delivery portion 604 remains implanted at the target tissue region 202 while the suture 614 extends outside the body.

These steps may be repeated for placement of each brachytherapy device 602, or multiple devices may be implanted as a group as further described below.

Although not illustrated, a locking member, such as the locking member 120 illustrated in FIGS. 2E and 27, may be used to secure the therapy device 602, e.g., the tail portion(s) 606, at one or both (see FIG. 2F) ends. Alternatively, the therapy device 602 may include securing elements such as the anchors 516 shown in FIG. 5. Still further, the therapy device 602 may be secured simply by folding and adhering the tail portions 606 to the breast 200 (see FIGS. 2E and 26).

After the desired dose of radiation has been delivered, the therapy delivery device 102 may be removed in any number of ways as already described herein, e.g., using a removal member, such as the tail portion 606, or a removal cannula.

FIG. 9A is an enlarged view of the therapy device 602 of FIGS. 6-7. As clearly illustrated in this view, the therapy device 602 may include the therapy delivery portion 604 and the tail portion 606. The therapy delivery portion 604 may include one, or preferably more, radioactive seeds 108 securely retained within the casing, e.g., heat-shrinkable tube 612. The tail portion 606 may be formed by the suture 614. The knot 616 of the suture 614 may be secured to the therapy delivery portion 604 by the heat shrinkable tube 612. While shown as utilizing spacers 110, they may not be required in some embodiments, e.g., the conformal properties of the casing, e.g., tube 612, may be sufficient to ensure proper seed 108 spacing and containment. FIG. 9B illustrates a section view of the seed 108 and tube 612 taken along line 9B-9B of FIG. 9A.

FIGS. 10A-10B illustrate a therapy device 1002 in accordance with another embodiment of the present invention. The device 1002 is similar in many respects to the device 602 described above. For example, the device 1002 may include a therapy delivery portion 1004 and a tail portion 1006. A casing, e.g., heat shrinkable tube 1012, may be used to encase the seeds 108 and optional spacers 110. Like the device 602, the tail portion 1006 may be formed by a suture 614 having a knot 616 that may be heat shrinkable to the therapy delivery portion 1004. However, unlike the device 602 of FIGS. 9A-9B, the tube 1012 may include a radioabsorptive portion 1014 positioned along a part of the circumference of at least the therapy delivery portion 1004 (see FIG. 10B). The radioabsorptive portion 1014, which may be formed integrally or separately with the tube 1012, may limit radiation exposure to tissue blocked by the radioabsorptive portion. FIG. 10B illustrates a section view of the seed 108 and tube 1012 taken along line 10B-10B of FIG. 10A.

FIGS. 11A-11B illustrate a therapy device 1102 in accordance with yet another embodiment of the present invention. The device 1102 is similar in many respects to the device 602 described above. For example, the device 1102 may include a therapy delivery portion 1104 and a tail portion 1106. A casing, e.g., heat shrinkable tube 1112, may be used to encase and constrain the seeds 108 and optional spacers 110. Like the embodiment illustrated in FIGS. 5A and 5B, the therapy device 1102 may incorporate an anchor member, e.g., anchor wire 1114, which extends along at least a part of the therapy delivery portion 1104 and protrudes from one or both ends. The anchor wire 1114 may be bent at one or both ends to form anchors 1116. When the therapy delivery portion 1104 exits the cannula 630 (see FIG. 8D), the anchors 1116 may extend and capture surrounding tissue, thereby assisting in preventing migration of the therapy device 1102. FIG. 11B illustrates a section view of the seed 108 and tube 1112 taken along line 11B-11B of FIG. 11A.

It is to be understood that any of the various components of the invention described herein may be used interchangeably with any of the described methods and systems. For example, any one of the devices 102, 402, 502, 602, 1002, and 1102 could be used with the methods described in FIGS. 2A-2E, 2F, and 8A-8E without departing from the scope of the invention.

The embodiments described above utilize a therapy delivery portion (e.g., portion 104 of FIG. 1 or portion 604 of FIG. 6) formed primarily by the shrink fit tube (e.g., tube 612 of FIG. 9A) and seeds 108. However, other embodiments of the therapy delivery portion may include an additional support member. The support member may be any material that lends support to the therapy delivery portion, e.g., a strip of material such as stainless steel or superelastic nickel titanium alloy. In addition to partially supporting the seeds 108, the material of the support member may divide the therapy delivery portion into a radiotransparent portion and a radioabsorptive portion. That is, it may partially surround at least a portion of the seeds 108 to provide some degree of attenuation or shielding of radiation to surrounding tissue. As a result, tissue on a side of the support member opposite the seeds 108 may receive a lower dose of radiation than tissue on the seed side. The support member may be enclosed within the casing, e.g., heat-shrinkable tube 112 or 612.

For example, FIGS. 12A and 12B illustrate a therapy device 1202 having a tail portion 1206 and a therapy delivery portion 1204 with a plurality of seeds 108 and a straight support member 1210 (see FIG. 12A). The support member 1210 may have a curved, e.g., arc-shaped, cross-section (see FIG. 12B). Alternatively, a relatively flat cross-section (not shown) may be provided. Other embodiments may utilize most any other cross-sectional shape, e.g., v-shaped. The support member 1210 may also have a variety of leading edge shapes including the shovel-tip shape illustrated in FIG. 12A. Some or all of the support member 1210 may be encased within a casing, e.g., heat shrinkable tube 1212, as already described above.

While the support member 1210 of FIG. 12A is generally straight, other support members in accordance with the present invention may be curved, e.g., may have some degree of curvature. For example, FIG. 13A illustrates a therapy device 1302 having a therapy delivery portion 1304 with a curved support member 1310 that imparts an arc- or otherwise curved-shape to the delivery portion 1304.

The support member 1310 may be formed to have curvature in its relaxed state or may simply be sufficiently flexible to permit curved implantation. As with the support member 1210 of FIGS. 12A-12B, the support member 1310 may have most any cross-sectional shape, e.g., flat, curved (as shown in FIG. 13B), V-shaped, etc. Some or all of the support member 1310 may be encased within a casing, e.g., heat shrinkable tube 1312, generally identical to the casings already described above. FIG. 13B illustrates a section view taken along line 13B-13B of FIG. 13A.

While not illustrated herein, support members in accordance with the present invention may include one or more slots, e.g., along a centerline, so that seeds may be placed at least partially within the slot. As a result, a therapy delivery portion that offers more rigidity than the unsupported therapy delivery portions described herein may be obtained while ensuring tissue on both sides of the support member receives radiation treatment.

FIGS. 14A-14B illustrate another exemplary embodiment of a therapy delivery portion 1404. In this embodiment, the therapy delivery portion includes a catheter or casing, e.g., tube 1412, having one or more lumens. A first or main lumen 1408 may receive the seeds (not shown), while a second lumen 1414 may contain an attenuating or shielding element 1416 extending over a longitudinal length of the tube 1412. As a result, the tube 1412 may have a radiotransparent portion (that portion not blocked by the element 1416), and a radioabsorptive portion (that portion shielded by the element 1416). In one embodiment, the tube 1412 can be made by co-extruding plastic (e.g., fluoropolymer) with an attenuating material such as strands of fine metallic wire (e.g., stainless steel, gold). In another embodiment, the attenuating material may be a coextrusion of polymer loaded with an attenuating material such as Tungsten powder. The tube 1412 may or may not be heat-shrinkable. For versatility, the shielding element 1416 may be straight or preformed in a curve. FIG. 14B illustrates a section view taken along line 14B-14B of FIG. 14A.

FIG. 15 is a partial view of an exemplary brachytherapy apparatus 1500 having a therapy device 1502 and catheter, e.g., cannula 1501, wherein the device 1502 includes a curved therapy delivery portion 1504, and a tail portion 1506. Other components of the system, e.g., pusher member and sharp obturator, are not illustrated in this view. The curved therapy delivery portion 1504 may be formed by a curved support member such as support member 1310 of FIG. 13A. The cannula 1501 preferably has a lumen diameter sufficiently large to accommodate the curved therapy delivery portion 1504 when the latter is constrained in a straightened configuration for delivery. Alternatively, the cannula 1501 may be sized to receive the therapy delivery portion 1504 when the latter is in its curved configuration. In still yet other embodiments, the therapy delivery portion 1504 may be generally straight but flexible and the cannula 1501 used to deliver the therapy delivery portion may be curved.

Figure 16A:
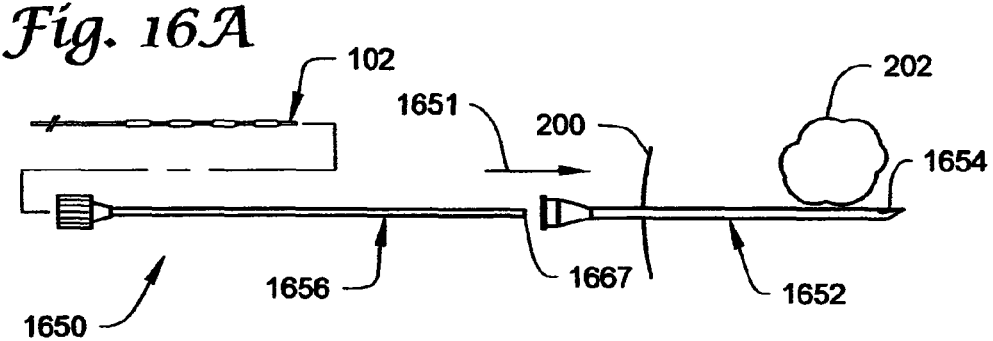
FIGS. 16A-16G are diagrammatic illustrations of non-linear brachytherapy apparatus and methods in accordance with various embodiments of the invention, where
Figure 16B:
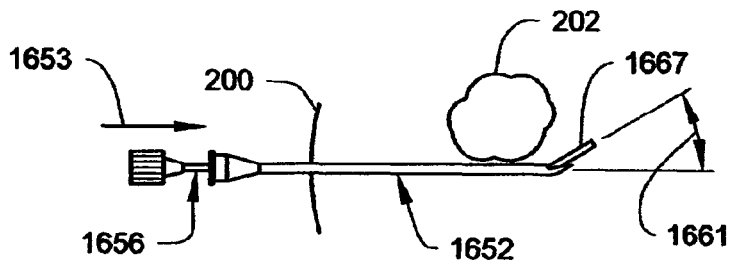

Non-linear (e.g., curved) catheters may also be used for delivery and placement of the brachytherapy devices described herein to regions and positions inaccessible to straight catheters. For example, FIGS. 16A-16E illustrate an exemplary apparatus 1650 and method operable to implant a brachytherapy device, e.g., device 102 of FIG. 1, along a non-linear axis. FIG. 16A illustrates the apparatus 1650 including a first catheter member, e.g., needle 1652, a second catheter member, e.g., flexible catheter 1656, and a brachytherapy device 102. The needle 1652 includes an off-axis opening 1654 at or near a distal end of the needle. The needle 1652 may be inserted into the body 200, in the direction 1651, until the distal end is positioned past the target tissue region 202 as shown in FIG. 16A. The flexible catheter 1656 may then be inserted through the needle 1652 (in the direction 1653) until a distal end 1667 of the catheter 1656 protrudes from the opening 1654 of the needle 1652 at an angle 1661 as shown in FIG. 16B. That is, an axis of the catheter 1656 may intersect, or be otherwise nonparallel to, an axis of the needle 1652.

The angle 1661 between the axes may vary, but angles ranging from greater than about 0 degrees to about 90 degrees, and more preferably about 5 degrees to about 35 degrees, are contemplated.

Figure 16C:
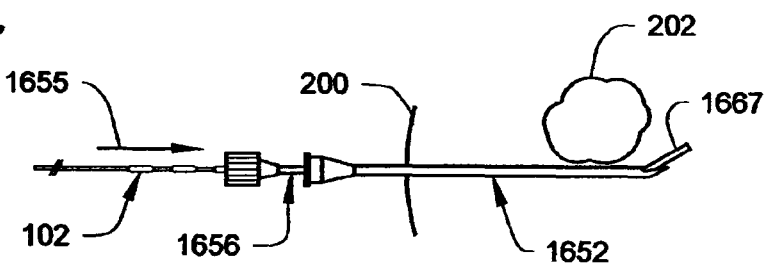

The device 102 may then be threaded through the catheter 1656 (in the direction 1655), as shown in FIG. 16C, until the therapy delivery portion of the device 102 is located at or near the distal end 1667 of the catheter 1656.

Figure 16D:
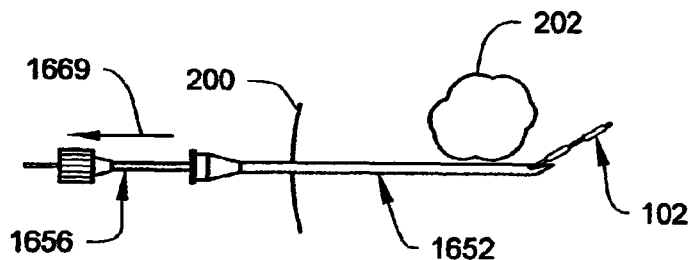
Figure 16E:
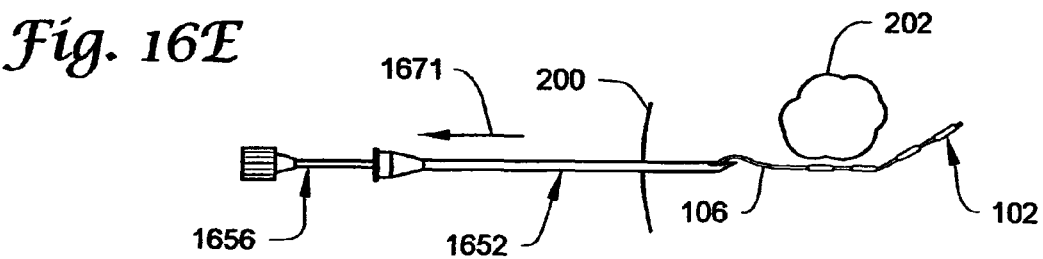

At this point, the catheter 1656 may be withdrawn slightly (in the direction 1669) as shown in FIG. 16D, exposing the therapy delivery portion of the device 102. The needle 1652 and catheter 1656 may then be withdrawn (in the direction 1671) from the body 200 together as shown in FIG. 16E. The device 102 is then implanted on a non-linear axis with its tail portion 106 extending outside the body as generally described above with reference to other embodiments (see e.g., FIGS. 2A-2E).

The ability to implant the device 102 along a non-linear axis may be beneficial in many applications. For example, where the target tissue region 202 is a breast lesion or a lumpectomy cavity in the breast, the non-linear device 102 may provide the capability to better focus radiation. Further, non-linear positioning may permit implantation around obstructions in the body. For example, in prostate brachytherapy, the region 202 could be a pubic arch around which the clinician desires to place radiation sources. While described above with respect to devices 102, the non-linear placement of FIGS. 16A-16E could also be used to implant individual radiation sources.

Figure 16F:
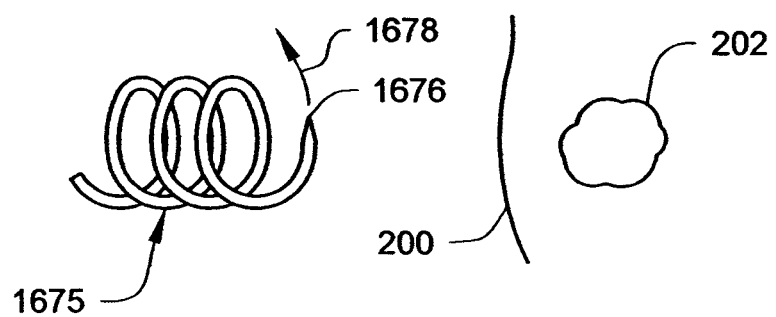
Figure 16G:
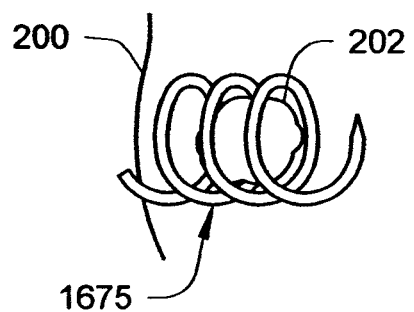

In yet other embodiments of non-linear placement apparatus and techniques, the needle 1652 of FIGS. 16A-16E may be replaced with a more spiral-shaped needle 1675 as shown in FIGS. 16F and 16G. While the actual needle size may vary depending on target tissue volume, needles having a helix diameter of about 3 centimeters (cm) are contemplated. The needle 1675 may be advanced into the body 200 in much the same way a corkscrew is inserted into a cork. That is, the needle 1675 may be rotated in a direction 1678 such that a sharp end 1676 penetrates the body 200 as indicated in FIG. 16F. FIG. 16G illustrates the needle 1675 once it is fully inserted. A flexible catheter (not shown) and therapy device (also not shown) may then be passed through the needle 1675 in much the same way as the catheter 1656 and device 102 are described with reference to FIGS. 16A-16E. The needle 1675 may then removed ("unscrewed"), leaving the therapy device in a spiral configuration around the target tissue region 202 (not illustrated).

When non-linear, e.g., off-axis, curved, and spiral, therapy delivery portions are used, the total number of therapy devices required to treat a given target tissue region may potentially be reduced as a result of the delivery portions' conformance to the shape of the target tissue. For example, in the case of curved delivery portions, several devices may be placed to curve around the target tissue region, effectively focusing radiation on a central area. This may result in lower dose exposure outside of the target tissue area, and potentially improved dose coverage within the target tissue. In the case of a spiral therapy delivery portion, a single therapy device of sufficient length may deliver adequate treatment by spiraling (e.g., forming a helix) around or within the target tissue region.

FIGS. 17A-17B illustrate an apparatus 1600 similar in most respects to apparatus 600 of FIG. 6. For instance, it may include a therapy device 1602 having a therapy delivery portion 1604 with seeds 108, and tail portion formed by a suture 1614. The suture 1614 may pass through a pusher member 1620 and the combined pusher member 1620 and delivery device 1602 may be placed within a cannula 1630. Unlike the cannula 630, however, the cannula 1630 may have a cutout 1634, e.g., the cannula may have a C-shaped cross section, as shown more clearly in FIG. 17B, over at least a portion of its length. While shown as straight, the cannula 1630 may also be curved. The cutout configuration may protect certain surrounding tissues/organs, e.g., skin, chest wall, liver, heart, during implantation. FIG. 17B is a cross-section taken along line 17B-17B of FIG. 17A with the therapy delivery device 1602 also shown in broken lines.

Figure 18:
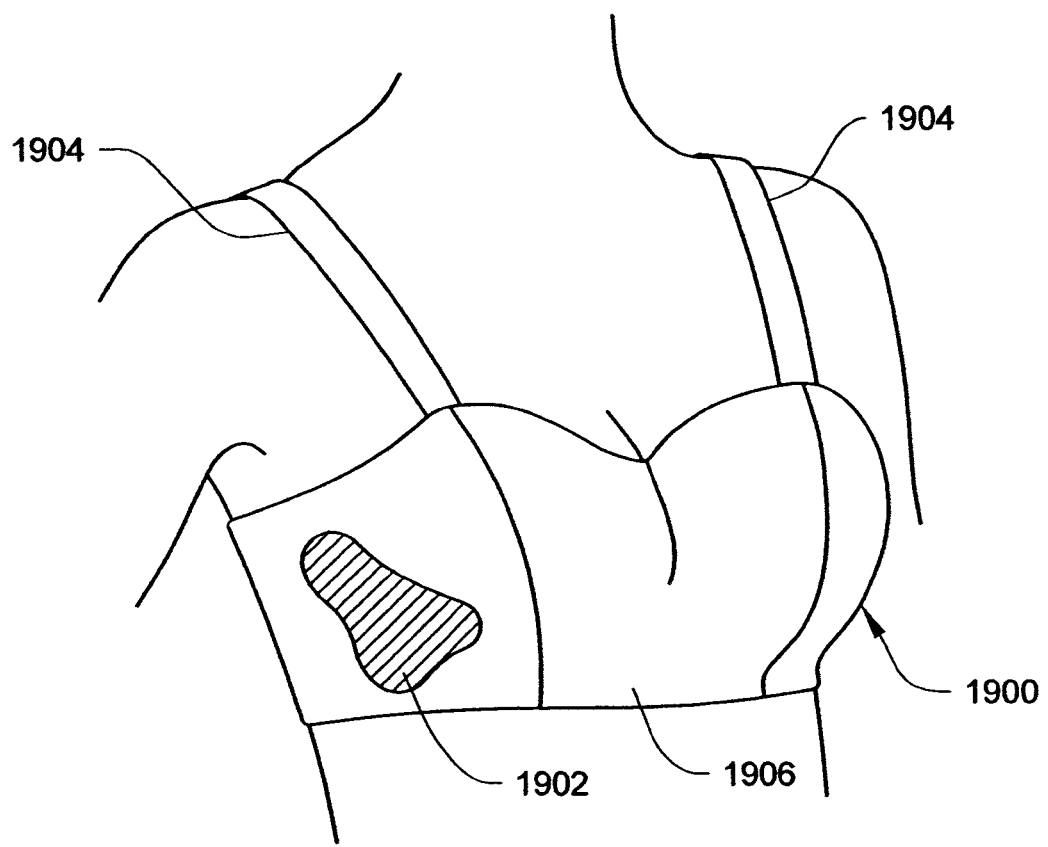
FIG. 18 is a view of a radiation attenuating garment, e.g., brassiere, in accordance with one embodiment of the invention.

During implantation of any of the devices described herein, the patient may optionally wear a protective garment, e.g., a chest covering brassiere or binder 1900, such as that illustrated in FIG. 18. The brassiere/binder 1900 may be similar in many respects to those garments described, for example, in U.S. Pat. No. 3,968,803 to Hyman; U.S. Pat. No. 5,152,741 to Farnio; and U.S. Pat. No. 5,538,502 to Johnstone. That is, it may include a partial body covering that secures via fasteners, e.g., shoulder straps 1904, to cover a portion of the chest (or other area surrounding the target tissue region). However, in addition to a fabric portion 1906, the binder 1900 may include a lining made from a radiation attenuating material 1902, e.g., lead, stainless steel, Tungsten. Such a garment may offer an added degree of shielding and permit greater patient mobility, while the radioactive sources, e.g., seeds 108, are indwelling, in an out-patient setting. The garment 1900 may be provided separately, or as part of a brachytherapy kit, e.g., kit 100.

Although discussed above primarily with respect to LDR brachytherapy, apparatus and/or methods of the present invention may also find use in HDR applications. For example, the tube 1412 of FIGS. 14A-14B may be used as a shielded delivery catheter for HDR treatment, e.g., the tube 1412 may be located in the body and a conventional HDR source (e.g., afterload HDR cable) of smaller diameter may be passed through the main lumen 1408. The attenuating element 1416 in the wall of the catheter (along a circumferential portion extending from about 10 o'clock to about 2 o'clock, for example) may attenuate the radiation exposure of regions vulnerable to radiation while the non-shielded section of the tube 1412 (along a circumferential portion extending from about 2 o'clock to about 10 o'clock) would allow exposure to the target tissue.

Further, for example, HDR radiation sources may be passed through a catheter, e.g., the cannula 1630 of FIGS. 17A and 17B, whereby the HDR radiation sources may be partially shielded from surrounding tissue by the geometry of the cannula 1630, e.g., the cutout 1634.

Figure 19:
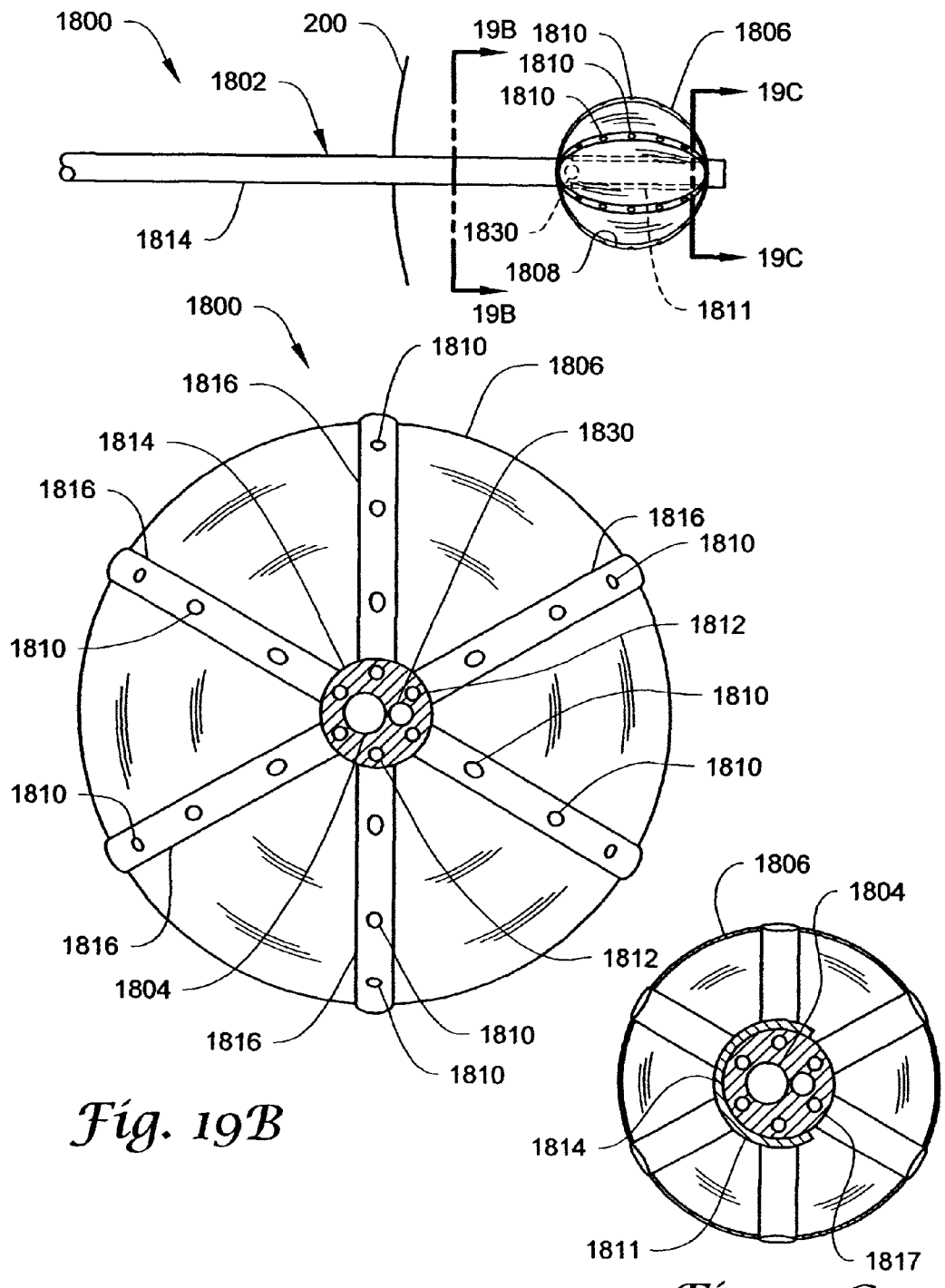
FIGS. 19A-19C are diagrammatic views of a balloon catheter assembly, e.g., HDR catheter, in accordance with one embodiment of the invention.

FIGS. 19A-19C illustrate incorporation of a HDR shielded catheter in accordance with the present invention on a balloon-type brachytherapy treatment device 1800. The device 1800 may be similar to the device disclosed in U.S. Pat. No. 5,913,813 to Williams et al. That is, it may include a brachytherapy catheter assembly 1802 having a catheter shaft 1814 with a proximal end and a distal end. An inflatable balloon 1806 may be coupled to the catheter shaft 1814 between the proximal end and the distal end. An inflation lumen 1830 may extend along the catheter shaft 1814 between the inflatable balloon 1806 and the proximal end to allow inflation of the balloon. A dose delivery lumen 1804 (see FIG. 19B) may also be provided and extend along the catheter shaft 1814 from the proximal end towards and the distal end, e.g., extending between the inflatable balloon 1806 and the proximal end.

In use, the distal end of the catheter shaft 1814 may be placed into a cavity, e.g., a lumpectomy cavity 1808 of breast 200, and the balloon 1806 inflated. A radiation source (not shown) may then be passed through the dose delivery lumen 1804, where it delivers radiation along a dose delivery portion of the catheter shaft, e.g., along a portion surrounded by the inflatable balloon 1806. By incorporating a radioabsorptive portion (e.g., arc-shaped member 1811 clearly illustrated in FIG. 19C) over the dose delivery portion of the catheter shaft 1814, only a predetermined portion, e.g., a window 1817, of the dose delivery portion may be relatively radiotransparent. As a result, the device 1800 may attenuate the radiation exposure of select areas, e.g., those close to the skin or chest wall, while delivering higher radiation levels to target tissue not blocked by the radioabsorptive portion 1811. While the radioabsorptive portion is illustrated herein as a separate member 1811 extending along a portion of the catheter shaft 1814, other embodiments may incorporate the radioabsorptive portion into the catheter shaft 1814 itself (see. e.g., the catheters described elsewhere herein such as the tube 1412 of FIGS. 14A-14B).

In some embodiments, the device 1800 may further include a vent system having one or more vents 1810 positioned around at least a portion of an outer surface of the balloon 1806. The vents 1810 may permit air and fluids within the cavity 1808 to escape as the balloon 1806 expands. One or more vent lumens 1812 (shown in FIG. 19B) associated with the catheter shaft 1814 may extend between the proximal end of the catheter shaft 1814 and the one or more vents 1810. The vents 1810 may fluidly communicate with one or more vent lumens 1812, thereby allowing the air and fluids to exit the body at the proximal end of the catheter shaft 1814 during and after balloon expansion.

In some embodiments, the external vents 1810 and vent lumens 1812 are formed by individual pieces of tubing 1816 attached to the balloon 1806 and catheter shaft 1814. In the vicinity of the balloon 1806, the tubing 1816 may be perforated to form the external vents 1810. The portion of the tubing 1816 located proximate the catheter shaft 1814 may or may not include perforations. The tubing 1816 may be formed of most any biocompatible material that can be securely attached to, or formed with, the balloon 1806 and catheter shaft 1814, e.g., silicone tubing.

Figure 20:
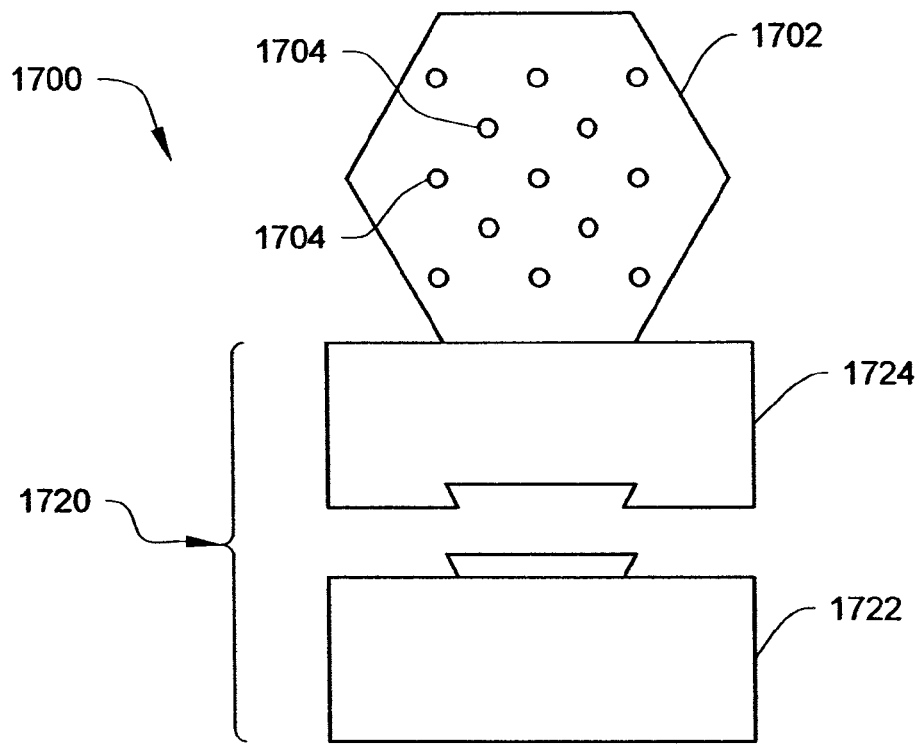
FIG. 20 is an exemplary embodiment of a delivery or implantation system for use with the brachytherapy methods and apparatus described herein.
Figure 21:
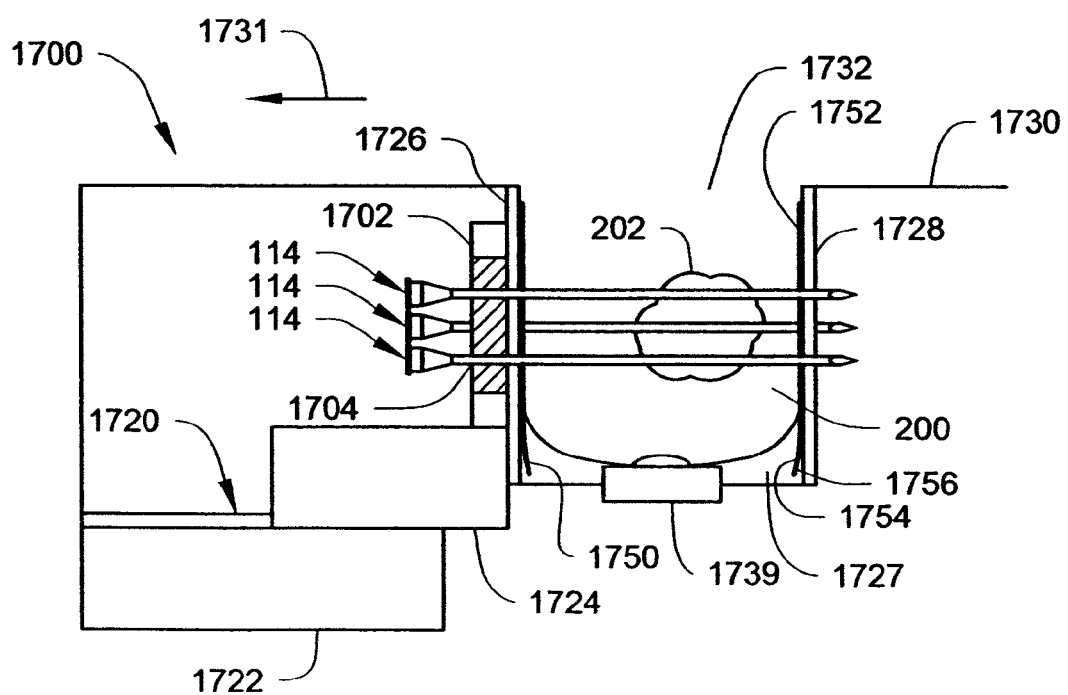
FIG. 21 is a diagrammatic view of the delivery system FIG. 20 as it may be used with the brachytherapy methods and apparatus described herein, e.g., the methods described in FIGS. 2A-2F and 8A-8E.
Figure 22:
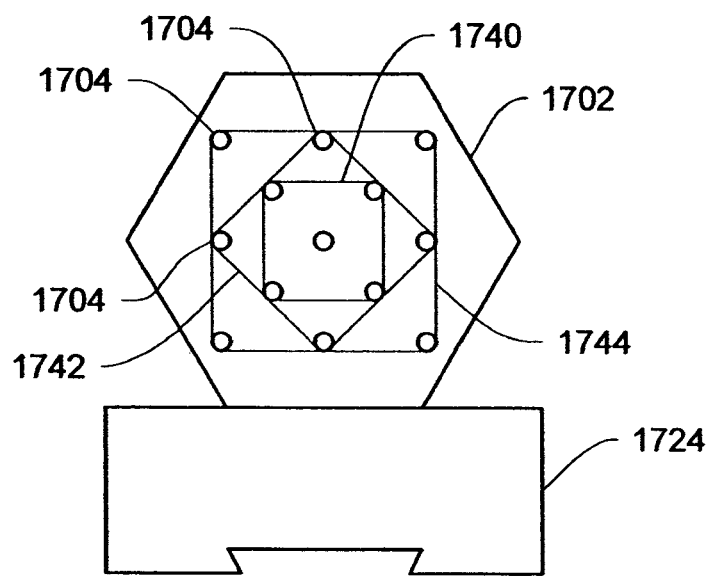
FIG. 22 is an enlarged view of an exemplary catheter, e.g., needle, guiding template for use with the delivery system of FIG. 21.

FIGS. 20-22 illustrate an exemplary system 1700 for implanting the LDR brachytherapy devices and their associated radiation sources described above to a target tissue region, e.g., the region surrounding a breast lumpectomy cavity. In the illustrated embodiment, the system includes a catheter or needle guiding template 1702 having a predetermined number and pattern (array) of openings 1704 as shown in FIG. 20. The template 1702 may form part of an adjustable catheter or needle guiding apparatus by coupling to a stereotactic table 1720, which is diagrammatically illustrated in the figures by base portion 1722, and translating portion 1724 (portions 1722 and 1724 shown exploded in FIG. 20). The stereotactic table 1720 is preferably coupled or attached to a patient locating or treatment surface 1730, e.g., patient table.

The template 1702 may be coupled to, or otherwise associated with, a first compression member 1726 located adjacent an opening 1732 in the treatment surface 1730. An opposing second compression member 1728 may be located on an opposite side of the opening 1732. The compression members 1726 and 1728 may be oriented about 90 degrees from a set of optional compression plates 1727 (only one plate 1727 shown).

One or both compression members 1726, 1728 may include a hole pattern similar to that of the template 1702, or may otherwise at least permit the passage of the needles/cannulae (e.g., needles 114 of FIG. 1) as illustrated in FIG. 21.

In use, a patient may lie on the treatment surface 1730, e.g., with the patient's head located in the direction 1731, such that the breast 200 passes through the opening 1732 of the treatment surface 1730. The optional compression plates 1727 may then be used to immobilize the breast 200.

Once the breast 200 is immobilized, the stereotactic table 1720, with the template 1702 attached, may be positioned, and the translating portion 1724 moved, until the compression members 1726 and 1728 contact the breast 200. The position of the stereotactic table 1720, and thus the needle guiding template 1702, may be aligned with the location of the target tissue region 202 via the use of various imaging techniques including, for example, X-ray, ultrasound and CT scan. In some embodiments, the template 1702 may be aligned relative to the target tissue region based upon input provided by an imaging device, e.g., a side viewing ultrasound apparatus 1739, located underneath the breast 200.

With the template 1702 aligned with the target tissue region 202 and positioned against the breast 200, one or more needles 114 may be inserted into the openings 1704. In the treatment of breast lesions, the needles 114 may be inserted completely through the breast 200 as illustrated in FIG. 21. Alternatively, and in the treatment of other cancers, the length of each needle 114 may be varied to ensure the correct depth penetration at each opening 1704, or the insertion depth of each needle 114 may simply be varied.

Certain embodiments of the system 1700 may optionally include an adhesive bandage member 1750 associated with the first compression member 1726, and/or an adhesive bandage member 1752 associated with the second compression member 1728. Preferably, the bandage members 1750 and 1752 are located between the respective compression members and the breast 200. The bandage members 1750 and 1752 may have adhesive on each side, e.g., a first side 1754 and a second side 1756, and include openings (not shown) that correspond generally to the openings 1704 of the template 1702. Alternatively, the bandage members 1750 and 1752 may be punctured by the needles 114 during needle insertion. When the compression members 1726 and 1728 are pressed against the breast 200, the bandage members 1750 and 1752 may adhere to the breast 200 and provide a dressing for the punctures created by the needles 114.

Once the needles 114 are inserted, the brachytherapy devices described herein, e.g., devices 102 or 602, may be inserted, and the needles 114 removed, in accordance with various methods as described and illustrated herein. For example, the brachytherapy devices 102 (or devices 602) may be inserted and the needles 114 (or the cannulae 630) removed in accordance with the methods described herein and illustrated in FIGS. 2A-2E and 2F (or 8A-8E).

With the needles 114 removed, the template 1702 and contact plates 1726 and 1728 may be withdrawn from the breast 200, leaving the bandage members 1750 and 1752 adhered to the breast by their respective first adhesive sides 1754. The tail portions 106 may then be anchored, e.g., by using locking members such as members 120 illustrated in FIGS. 2E and 27.

A liner (not shown) may then be removed from the respective second adhesive side 1756 of each bandage member 1750 and 1752. Once the second adhesive side 1756 is exposed, the flexible tail portions 106 may be folded against the second adhesive side, where they adhere thereto. A second, single-sided adhesive member (not shown) may be placed over each bandage member 1750 and 1752 to secure the tail portions and cover any exposed adhesive on the second adhesive side 1756. As a result, the flexible tail portions may be folded against the contours of the breast and secured.

In some embodiments, the openings 1704 of the template 1702 may be grouped according to a particular target tissue volume, e.g., lesion size, as shown in FIG. 22. For example, a small square, five-opening pattern 1740 may be utilized for small target tissue regions (e.g., those regions up to about 1 centimeter in diameter), while a larger nine-opening pattern 1742 may be utilized for larger target tissue regions (e.g., those regions up to about 2 cm in diameter). A still larger, thirteen-opening pattern may be utilized for even larger target tissue regions (e.g., those regions up to about 3 cm in diameter).

By aligning the center opening of the template 1702 with the center of the target tissue region, the template may indicate a standard number of seeds, e.g., a particular number of therapy devices 102, based upon the predetermined target volume. This could simplify, or possibly eliminate, the need for complex dose mapping calculations commonly associated with conventional brachytherapy methods.

It is noted that the patterns 1740, 1742, and 1744 are exemplary only. In other embodiments, the patterns may include most any number of openings 1704 in most any shaped pattern, e.g., a circular array of 5 to 50 catheters. Moreover, the templates could accommodate more that one diameter catheter or needle (e.g., 10, 15, and 20 mm diameters). Moreover, while shown with three patterns, templates having most any number are possible without departing from the scope of the invention.

Figure 23:
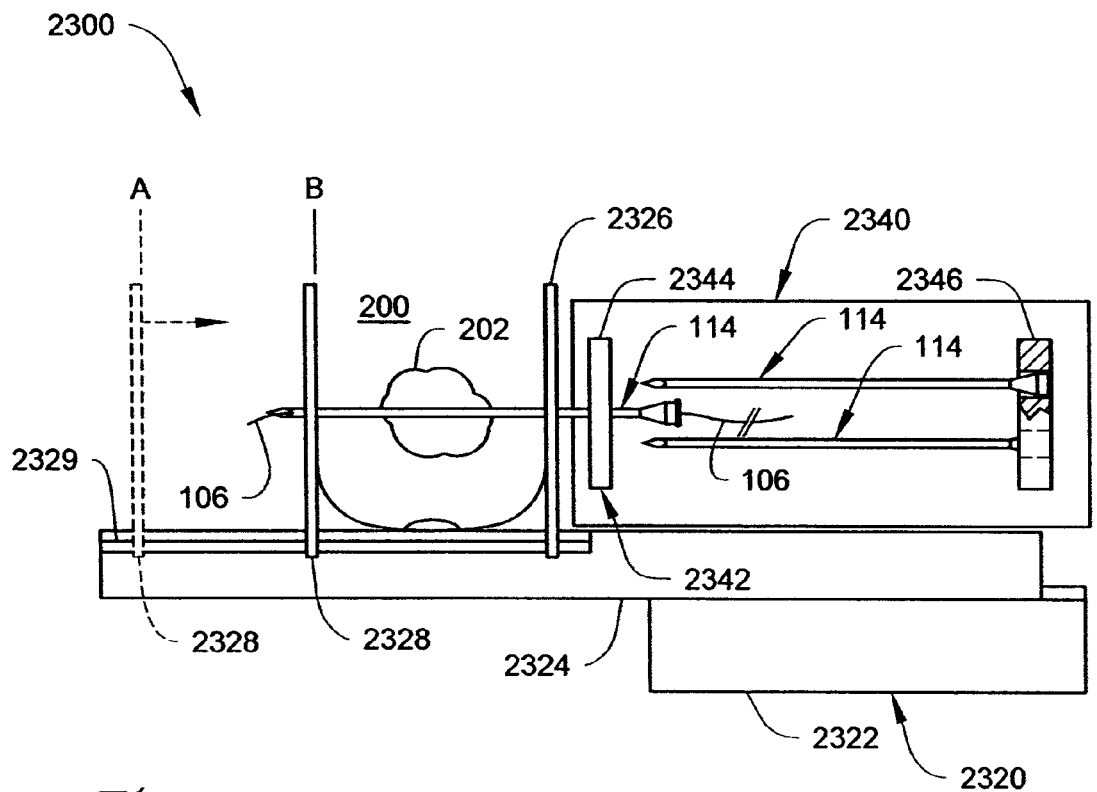
FIG. 23 is diagrammatic view of another delivery or implantation system for use with the brachytherapy methods and apparatus described herein.
Figure 24:
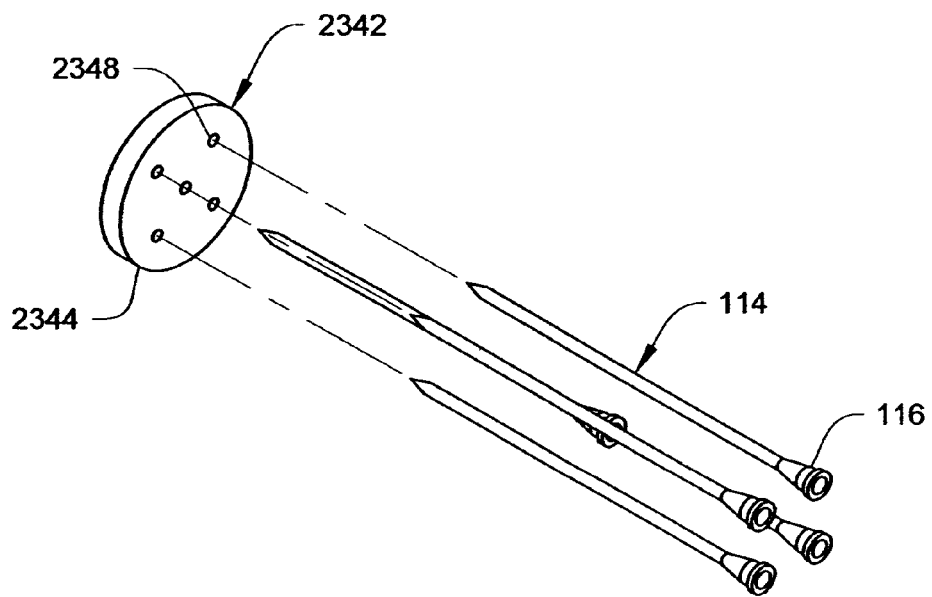
FIG. 24 is an exploded view of a portion, e.g., a cartridge, of the delivery system of FIG. 23.

FIGS. 23 and 24 illustrate another system for implanting brachytherapy devices of the present invention. FIG. 23 illustrates a system 2300 similar in many respects to the system 1700 described above. For instance, the system 2300 may include a stereotactic table 2320 secured to treatment surface, e.g., patient table (not shown). The table 2320 may include a base portion 2322 and a translational portion 2324. The system 2300 may also include a first or proximal compression member 2326 and a second or distal compression member 2328. One or both compression members 2326 and 2328 may be movable relative to the other and/or the base portion 2322, e.g., along a slide rail 2329.

Unlike the system 1700, however, the system 2300 may also include a catheter or needle cartridge receiver 2340 operable to receive a pre-assembled needle cartridge 2342 having multiple needles 114 positioned in a predetermined array. The needle cartridge 2342 is shown in an exploded view in FIG. 24. The cartridge 2342 may include a first holder 2344 and a second holder 2346 (second holder 2346 not shown in FIG. 24). The holders 2344 and 2346 may include holes 2348 to hold and guide the multiple needles 114 in the desired predetermined array during insertion. Where needles 114 include a hub 116, the holes 2348 in the holder 2346 may be larger than the corresponding holes 2348 in the holder 2344 to permit the passage of the hub 116 (see FIG. 23).

During operation of the system 2300, the stereotactic table 2320 may be aligned as described above with respect to the system 1700. Once aligned, the breast 200 may be immobilized with the compression members 2326 and 2328. Based upon the particular volume of the target tissue region 202, a specific cartridge 2342 may be selected and pre-assembled with a corresponding number of catheters, e.g., needles 114. For instance, the cartridge in FIG. 24 is a 5 catheter configuration. However, other cartridges may utilize more or less catheters (e.g., 9 catheter and 13 catheter cartridges). The cartridge 2342, including the holders 2344 and 2346 and the catheters 114, may then be loaded into the cartridge receiver 2340. Portions of the holders 2344 and 2346 may be designed to contact one or more internal surfaces of the cartridge receiver 2340 so that the cartridge 2342 aligns with the cartridge receiver upon insertion.

Once the cartridge 2342 is loaded, each needle 114 may be independently and manually advanced through the proximal compression plate 2326 (which may include a hole pattern identical to the holder 2344), the breast 200, and the distal compression member 2328. The central needle 114 may be advanced first and its position within the target tissue region 202 confirmed (or repositioned) before the remaining needles are advanced. Brachytherapy devices, e.g., devices 102 of FIG. 1, may then be placed into the needles 114 as described in FIGS. 2A-2E. Alternatively, the devices 102 could be preinstalled in the cartridge 2342.

With the devices 102 inserted completely, the distal tips of the tail portions, see e.g., tail portion 106 of FIG. 1, may be temporarily secured relative to the distal compression member 2328. At this point, the needles 114 may be retracted and removed from the breast 200, and ultimately, withdrawn from the cartridge loader 2340. The proximal compression member 2326 may then be withdrawn and the proximal tail portions secured to the breast using, for example, the locking devices 120 described above and illustrated in FIGS. 2E and 27. The distal compression member 2328 may then be withdrawn and the distal tail portions secured relative to the breast 200 in a similar manner.

Figure 25A:
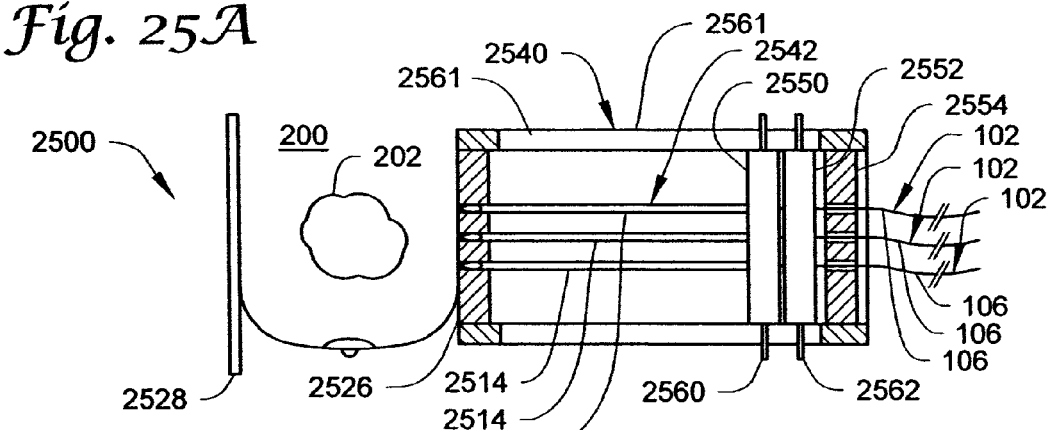
FIGS. 25A-25D are diagrammatic illustrations of a delivery or implantation system and method in accordance with yet another embodiment of the invention.

FIGS. 25A-25D illustrate yet another system and method for inserting the brachytherapy devices of the present invention into a target tissue region. FIG. 25A illustrates a system 2500 similar in many respects to the systems 1700 and 2300 described above. For example, the system 2500 includes a stereotactic table (not shown) having a catheter or needle cartridge receiver 2540 coupled thereto. The stereotactic table is preferably coupled to the treatment table (also not shown). The system 2500 may also include a catheter or needle cartridge 2542. The needle cartridge 2542 may include a series of needles 2514, e.g., 5, 9, or 13 needle array, which are generally rigidly and orthogonally mounted to a first plunger member 2550. In this embodiment, the needles 2514 may be hubless as the proximal ends of the needles 2514 are secured (e.g., press fit, staked, adhered, etc.) to the first plunger member 2550.

The cartridge 2542 may also include a first or proximal compression member 2526 (which may form the needle guiding template) as well as a second plunger member 2552 and an optional backing plate 2554. In other embodiments, the backing plate 2554 may be part of the cartridge receiver 2540. As with the systems previously described herein, the system 2500 may also include a second or distal compression member 2528 to assist in immobilizing the breast 200.

During operation, the stereotactic table may be aligned such that the center of the needle cartridge receiver 2540 is centered relative to the target tissue region 202. The cartridge 2542 may then be loaded into the cartridge receiver 2540, and the breast immobilized by the first and second compression members 2526 and 2528. The brachytherapy devices, e.g., devices 102 of FIG. 1, may have been previously loaded into the needles 2514 of the cartridge 2542. The first plunger member 2550 may then be advanced toward the breast 200. Because the needles 2514 are rigidly coupled to the first plunger member 2550, the needles 2514 advance simultaneously into the target tissue region of the breast 200 in the predetermined parallel array. The first plunger member 2550 may include a tab 2560 that rides along a slot or surface 2561 of the cartridge receiver 2540 so that the first plunger member 2550 may be manually or automatically advanced from outside the cartridge.

Figure 25B:
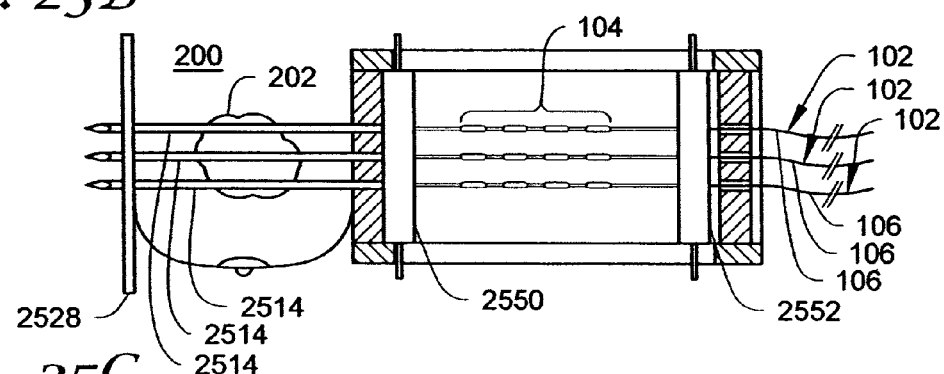
Figure 25C:
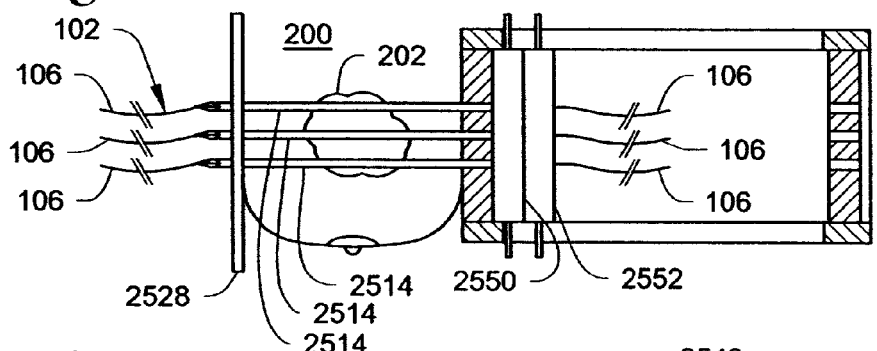

After the first plunger member 2550 has been fully advanced as shown in FIG. 25B, the second plunger member 2552 may be advanced toward the breast 200. The second plunger member 2552 has the proximal tail portions 106 of the brachytherapy devices 102 releasably secured thereto. Thus, advancing the second plunger member 2552 may advance one or more of the brachytherapy devices 102 into place such that the distal tail portions 106 emerge from the distal ends of the needles 2514 as shown in FIG. 25C.

Figure 25D:
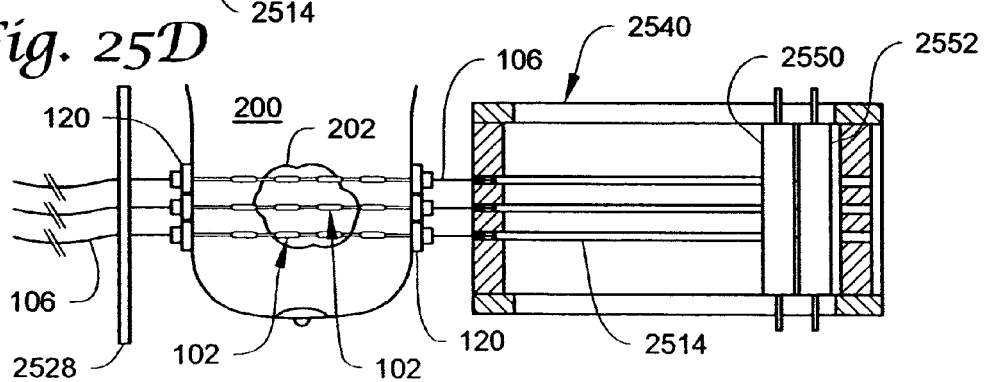

The distal tail portions 106 may temporarily be secured to the distal compression member 2528 to hold the brachytherapy devices 102 in place. Once the distal tail portions 106 are secured, the proximal tail portions 106 may be released from the second plunger member 2552 and the first and second plunger members 2550 and 2552 may be retracted as shown in FIG. 25D. The cartridge receiver 2540 may also be retracted so that the proximal tail portions 106 may be secured in accordance with methods already described herein (e.g., locking members 120). The distal tail portions 106 may then be disconnected from the distal compression member 2528 and the latter withdrawn. The distal tail portions 106 may then be secured relative to the breast 200.

Thus, the system 2500 provide an apparatus for simultaneously implanting, in a two dimensional array, multiple brachytherapy devices into the body. Moreover, the systems described herein allow simultaneously advancing a two-dimensional array of catheters into a target tissue region, and then delivering or implanting one or more radiation sources through at least one of the catheters of the array. Once the radiation sources are implanted, sequential or simultaneous removal of the catheters of the array of catheters from the target tissue region may be accomplished.

Figure 26:
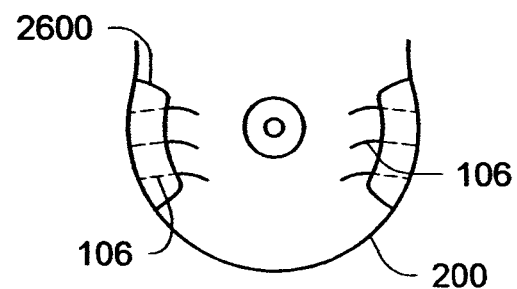
FIG. 26 is a view of a portion of a human body, e.g., a female breast, after the brachytherapy devices as described herein have been implanted and secured.

As already described above, some embodiments may permit the tail portions 106 to be secured to the breast using an adhesive pad or bandage 2600 as illustrated in FIG. 26. Here, the bandage may be used in conjunction with, or as an alternative to, the locking members 120.

To assist the health-care provider in securing the distal and/or proximal tail portions 106, the compression members 2526, 2528 may be configured as generally illustrated in FIG. 27. That is, openings 2570 in the plate (e.g., plate 2528) through which the tail portions 106 pass may include a recess 2572 that holds the locking member 120 against the skin. As a result, when the compression plate 2528 is withdrawn, the locking member 120 may already be threaded over the tail portion 106. The health care provider may then quickly crimp the locking member 120, e.g., along a deformable portion 2576.

The brachytherapy devices described herein may be implanted into (and/or around) the tumor prior to surgical excision (neoadjuvantly), and then subsequently removed before or at the time of surgery. Preferably, such treatments may shrink or even destroy the tumor. In other embodiments, the present invention may be used to deliver brachytherapy after surgical removal of the tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemo, EBRT.

The brachytherapy devices described herein may also be both indwelling and removable. In contrast, conventional LDR and HDR brachytherapy seeds are typically one or the other—LDR seeds are generally indwelling but not removable while HDR sources are generally removable but remain indwelling only momentarily. As a result, the present invention may allow brachytherapy treatment at radiation activity levels greater than those commonly associated with LDR treatment while also permitting removal of the radioactive source. Moreover, treatment in accordance with the present invention may avoid some of the disadvantages of HDR treatment, e.g., high activity, exposure of unintended tissue, potentially bulky and protruding catheters, and the need for numerous patient visits to receive treatment.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

Apparatus and methods of the present invention could also potentially achieve desired dosage with relatively few catheters. For example, apparatus and methods of the present invention could potentially obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

Apparatus and methods of the present invention may also provide other benefits to the patient. For example, potentially less skin damage and discomfort may result from smaller and more flexible catheter insertions. Further, the small flexible tail portions described herein may be folded and taped against the skin, unlike rigid HDR catheters. Thus, the patient may have less discomfort over the course of treatment and potentially improved post-procedural cosmesis. Further, for example, apparatus and techniques in accordance with the present invention may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems could potentially be reduced or eliminated with certain cancers (e.g., breast).

The complete disclosure of the patents, patent documents, and publications cited in the Background, the Detailed Description of Exemplary Embodiments, and elsewhere herein are incorporated by reference in their entirety as if each were individually incorporated.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A system for delivering brachytherapy to a target tissue region within a breast, the system comprising a plurality of elongate therapy devices, each therapy device comprising:
   an elongate tubular member comprising a tail portion including a proximal end, and a therapy delivery portion including a distal end sized for introduction through tissue of a breast to a target tissue region, and a first lumen extending between an opening in the proximal end and the distal end;
   a support member extending along the therapy delivery portion of the tubular member outside the first lumen without extending to the tail portion, the support member substantially fixed relative to the therapy delivery portion;
   the therapy delivery portion positionable in a curved configuration within the breast for delivery of radiation to the target tissue region, wherein the support member biases the target therapy portion for advancement through tissue in a straight configuration and allows deployment to the curved configuration within the target tissue region, the support member substantially maintaining the therapy delivery portion in a fixed or static position in the curved configuration when deployed within the target tissue region; and
   the tail portion sufficiently long to extend from the breast when the target delivery portion is introduced into the target tissue region of the breast,
   whereby the plurality of elongate therapy devices is advanceable through tissue until the therapy delivery portion of each of the tubular members is positioned within or around the target tissue region in the curved configuration, allowing a radiation source to be introduced into the first lumen of the each of the tubular members through the opening in the proximal end for delivering radiation therapy to the target tissue region.

2. The system of claim 1, wherein each therapy delivery portion is configured in the curved configuration to provide conformance of the therapy delivery portion to a shape of the target tissue region to be irradiated.

3. The system of claim 1, further comprising means for delivering the plurality of elongate therapy devices through tissue to the target tissue region.

4. The system of claim 3, wherein the means for delivering the plurality of elongate therapy devices comprises a plurality of tubular members for receiving respective therapy devices therethrough.

5. The system of claim 1, further comprising one or more radiation sources introduceable into the first lumen through the opening in the proximal end for delivering radiation therapy to the target tissue region.

6. The system of claim 5, wherein the one or more radiation sources comprise a plurality of radioactive seeds spaced apart along each of the therapy delivery portions.

7. The system of claim 5, wherein the one or more radiation sources comprise a HDR afterload cable.

8. The system of claim 1, wherein the tubular member comprises heat shrink tubing.

9. The system of claim 1, wherein the support member has curvature in its relaxed state.

10. The system of claim 1, wherein the support member is sufficiently flexible to permit curved implantation.

11. The system of claim 1, wherein the tubular member comprises a second lumen containing the support member.

12. The system of claim 1, wherein the support member is encased within the tubular member.

13. The system of claim 1, wherein the tubular member and support member comprise a plastic co-extrusion.

14. The system of claim 1, wherein the support member is configured for attenuating or shielding radiation to surrounding tissue.

15. The system of claim 1, wherein the support member comprises a strip of material.

16. The system of claim 1, wherein the support member has a cross-section defining a width extending transversely relative to the first lumen and a height orthogonal to the width, the height being smaller than the width.

17. The system of claim 16, wherein the support member is disposed adjacent the first lumen such that the width of the support member extends only partially around the first lumen.

18. The system of claim 1, wherein the support member has a flat cross-section.

19. The system of claim 1, wherein the support member has an arcuate cross-section.

20. An implantable brachytherapy treatment system for treating a target tissue region within a breast, comprising:
   at least one elongate tubular member comprising a proximal end, a distal end sized for introduction through tissue of a breast to a target tissue region, and a first lumen extending between an opening in the proximal end and the distal end; and
   a support member extending along a therapy delivery portion between the proximal end and distal end of the tubular member outside the first lumen, the support member substantially fixed relative to the therapy delivery portion, the support member offset asymmetrically relative to the first lumen for delivering the tubular member through tissue in a straight configuration and deploying the target delivery portion in a curved configuration within or around the target tissue region, wherein the support member biases the therapy delivery portion for advancement through tissue in a straight configuration and allows deployment to the curved configuration within the target tissue region; and
   a radiation source receivable in the first lumen of the tubular member through the opening in the proximal end for delivering radiation therapy to the target tissue region in the curved configuration after the target delivery portion has been introduced into the target tissue region.

21. The system of claim 20, wherein the support member substantially maintains the therapy delivery portion in a fixed or static position in the curved configuration when deployed within the target tissue region.

22. The system of claim 20, wherein the wherein the at least one tubular member comprises heat shrink tubing.

23. The system of claim 20, wherein the support member is enclosed within the tubular member along the therapy delivery portion.

24. The system of claim 20, wherein the tubular member comprises a second lumen extending along the therapy delivery portion adjacent the first lumen, and wherein the support member is substantially fixed within the second lumen.

25. The system of claim 20, wherein the support member comprises a strip of material.

26. The system of claim 20, wherein the support member is configured for attenuating or shielding radiation to surrounding tissue.

27. The system of claim 20, wherein the support member has curvature in its relaxed state, the system further comprising a cannula for constraining the tubular member in the straight configuration for introduction through tissue.

28. The system of claim 20, wherein the radiation source comprises an afterload HDR cable.

29. The system of claim 20, wherein the support member has a flat cross-section.

30. The system of claim 20, comprising a plurality of tubular members including the at least one tubular member, the plurality of tubular members configured for simultaneous introduction through tissue of a breast to a target tissue region in a straight configuration and deployable in a curved configuration within or around the target tissue region.

* * * * *